(12) United States Patent
Berzofsky et al.

(10) Patent No.: US 9,394,352 B2
(45) Date of Patent: Jul. 19, 2016

(54) IMMUNOGENIC POTE PEPTIDES AND METHODS OF USE

(71) Applicant: The United States of America, as represented by the Secretary, Department of Health and Human Services, Washington, DC (US)

(72) Inventors: Jay A. Berzofsky, Bethesda, MD (US); Yi-Hsiang Huang, Taipei (TW); Masaki Terabe, Potomac, MD (US); Ira H. Pastan, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 121 days.

(21) Appl. No.: 14/496,194

(22) Filed: Sep. 25, 2014

(65) Prior Publication Data

US 2015/0010590 A1 Jan. 8, 2015

Related U.S. Application Data

(60) Division of application No. 13/610,421, filed on Sep. 11, 2012, now Pat. No. 8,871,902, which is a continuation-in-part of application No. PCT/US2011/027577, filed on Mar. 8, 2011.

(60) Provisional application No. 61/313,559, filed on Mar. 12, 2010.

(51) Int. Cl.
| | |
|---|---|
| C07K 7/06 | (2006.01) |
| C07K 14/47 | (2006.01) |
| A61K 39/00 | (2006.01) |
| A61K 48/00 | (2006.01) |

(52) U.S. Cl.
CPC .......... *C07K 14/4748* (2013.01); *A61K 39/0011* (2013.01); *A61K 48/00* (2013.01); *A61K 2039/55516* (2013.01); *A61K 2039/55522* (2013.01); *A61K 2039/55538* (2013.01); *A61K 2039/57* (2013.01); *C12N 2730/10111* (2013.01)

(58) Field of Classification Search
None
See application file for complete search history.

(56) References Cited

U.S. PATENT DOCUMENTS

| | | |
|---|---|---|
| 6,586,570 B1 | 7/2003 | Frudakis et al. |
| 7,541,035 B2 | 6/2009 | Berzofsky et al. |
| 2004/0081653 A1 | 4/2004 | Raitano et al. |
| 2009/0208518 A1 | 8/2009 | Berzofsky et al. |

FOREIGN PATENT DOCUMENTS

| | | |
|---|---|---|
| WO | WO 03/013431 | 2/2003 |
| WO | WO 2004/016733 | 2/2004 |
| WO | WO 2005/080436 | 9/2005 |

OTHER PUBLICATIONS

Bera et al., "POTE, a highly homologous gene family located on numerous chromosomes and expressed in prostate, ovary, testis, placenta, and prostate cancer," *Proc. Natl. Acad. Sci. USA* 99(26):16975-16980, 2002.
Bera et al., "POTE paralogs are induced and differentially expressed in many cancers," *Cancer Res.* 66(1):52-56, 2006.
Berzofsky et al., "Strategies for designing and optimizing new generation vaccines," *Nat. Rev. Immunol.* 1(3):209-219, 2001.
Copeland et al. (UniProt database ID—A5WCM1_PSYWF, Complete sequence of chromosome of *Psychrobacter* sp. PRwf-1, US DOE Joint Genome Institute, integrated into UniProt database on Jul. 10, 2007).
Das et al., "Palmitoylation of POTE family proteins for plasma membrane targeting," *Biochem. Biophys. Res. Commun.* 363(3):751-756, 2007.
Gross et al., "High vaccination efficiency of low-affinity epitopes in antitumor immunotherapy," *J. Clin. Invest.* 113(3):425-433, 2004.
Hrbek et al., "A Phylogenetic and Biogeographic Perspective on the Evolution of Poeciliid Fishes," *Mol. Phylogenet. Evol.*, 43:986-998, 2007.
Ise et al., "Expression of POTE protein in human testis detected by novel monoclonal antibodies," *Biochem. Biophys. Res. Commun.* 365(4):603-608, 2008.
Ward et al., "Three Genomes from the Phylum Acidobacteria Provide Insight into the Lifestyles of These Microorganisms in Soils," *Appl. Environ. Microbiol.*, 75:2046-2056, 2009.

*Primary Examiner* — Brad Duffy
*Assistant Examiner* — Nelson B Moseley, II
(74) *Attorney, Agent, or Firm* — Klarquist Sparkman, LLP

(57) ABSTRACT

POTE has recently been identified as a tumor antigen expressed in a variety of human cancers, including colon, ovarian, breast, prostate, lung and pancreatic cancer. Described herein are immunogenic POTE polypeptides, including modified POTE polypeptides, that bind MHC class I molecules. The immunogenic POTE polypeptides are capable of inducing an immune response against POTE-expressing tumor cells. Thus, provided herein is a method of eliciting an immune response in a subject, such as a subject having a type of cancer that expresses POTE.

18 Claims, 16 Drawing Sheets

AAD/POTE 553

AAD/POTE 553-1Y

AAD/POTE 553-2L

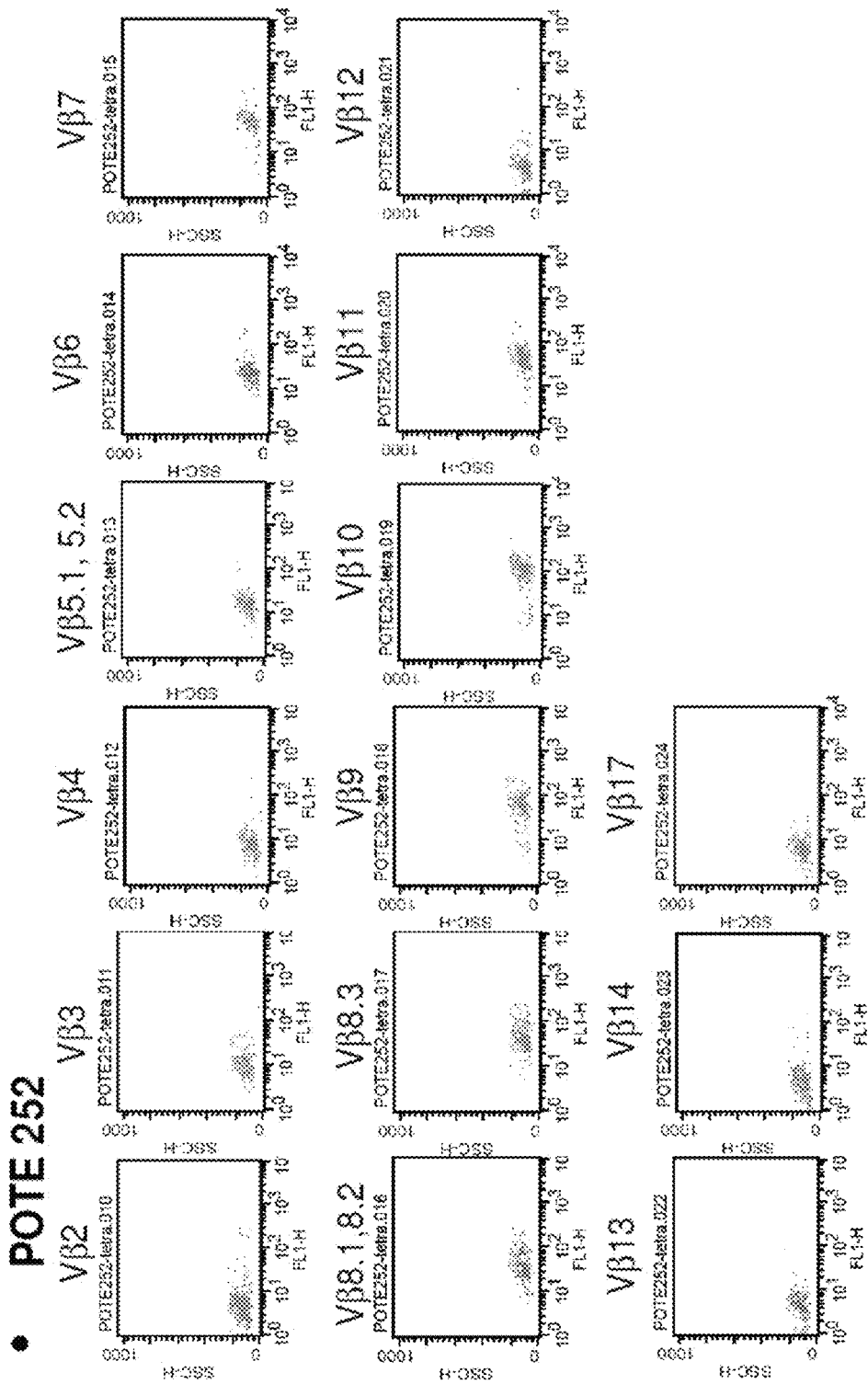

IMMUNOGENIC POTE PEPTIDES AND METHODS OF USE

CROSS REFERENCE TO RELATED APPLICATIONS

This is a divisional of U.S. application Ser. No. 13/610,421, filed Sep. 11, 2012, which is a continuation-in-part of PCT/US2011/027577, filed Mar. 8, 2011, which claims the benefit of U.S. Provisional Application No. 61/313,559, filed Mar. 12, 2010. The above-listed applications are herein incorporated by reference in their entirety.

FIELD

This disclosure concerns POTE peptides, including modified POTE peptides, and their use for stimulating an immune response, such as for the treatment of cancer.

BACKGROUND

Breast and prostate cancers are the most frequently diagnosed malignancies in the United States. Generally these cancers cannot be curatively resected, except when detected early. Other non-surgical approaches, such as radiotherapy or chemotherapy, also affect normal cells and result in side effects that limit treatment. In addition, all treatments for recurrent or metastatic cancer are palliative. Consequently, development of novel systemic approaches to treat advanced, recurrent or metastatic cancer is needed. Immunotherapy may have great potential as a promising treatment for cancer patients because of its specificity and freedom from toxic effects of chemotherapies.

CD8+ cytotoxic T lymphocytes (CTLs) can recognize and specifically kill tumor cells expressing peptides from tumor-associated antigens presented by major histocompatibility complex (MHC) class I molecules. Therefore, most current cancer immunotherapy strategies focus on induction of CTLs that lyse tumor cells. Antigen-specific cancer immunotherapy often relies on identification of epitopes expressed by cancer cells that can be used as targets for CD8+ T cells. However, the natural CTL epitopes of cancers are not always optimal because the CTL repertoire against high-affinity epitopes is often tolerized (Gross et al., *J. Clin. Invest.* 113(3):425-433, 2004). Epitope enhancement, by means of modification of the amino acid sequence of epitopes, was developed to improve the efficacy of vaccines primarily through increasing affinity of peptide for MHC molecules (Berzofsky et al., *Nat. Rev. Immunol.* 1(3):209-219, 2001).

Discovering tumor-specific antigens is critical to the development of effective cancer immunotherapy. Recently, a novel tumor associated antigen, POTE, was identified from several kinds of human cancers (Bera et al., *Proc. Natl. Acad. Sci. USA* 99(26):16975-16980, 2002; Bera et al., *Cancer Res.* 66(1):52-56, 2006). This tumor antigen is called POTE because its expression was first identified in normal prostate, ovary, testis, and placenta tissues, as well as in prostate cancer. The POTE gene family was found dispersed among eight different chromosomes (2, 8, 13, 14, 15, 18, 21, and 22) with different mRNA length. Nevertheless, the POTE cDNA sequence among various chromosomes is highly homogeneous with the divergence less than 10%. Subsequent studies revealed that POTE genes were expressed not only in prostate cancer, but also in a wide variety of human malignancies, including breast, colon, lung, ovary and pancreas. There are distinct patterns of expression of POTE in normal tissues and cancers. Among the various cancers, the POTE paralogs on chromosome 2 (POTE-2γ) are the most frequently expressed.

Because POTE mRNA is detectable only in a limited number of normal human tissues (prostate and testis in the male, and ovary and placenta in the female), the POTE protein is considered as a member of the cancer-testis antigen family. Expression of cancer-testis antigens in the placenta or testis should not lead to T-cell activation because of the very low expression of MHC class I molecules in these tissues. Therefore, the POTE antigen is a potential target for the immunotherapy of cancers, including breast and prostate cancers.

SUMMARY

POTE has recently been identified as a tumor antigen expressed in a variety of human cancers, including colon, ovarian, breast, prostate, lung and pancreatic cancer. Thus, disclosed herein are immunogenic POTE polypeptides, including modified POTE polypeptides, that bind MHC class I molecules. The immunogenic POTE polypeptides are capable of inducing an immune response against POTE-expressing tumor cells.

Provided herein are immunogenic POTE polypeptides comprising no more than 10 consecutive amino acids of a POTE protein. In some embodiments, the POTE polypeptides are modified to alter their binding affinity to MHC class I molecules. Fusion proteins including the immunogenic POTE polypeptides, compositions including the immunogenic POTE polypeptides and nucleic acid molecules and vectors encoding the immunogenic POTE polypeptides are also provided.

Further provided is a method of eliciting an immune response in a subject by selecting a subject in need of treatment and administering to the subject a therapeutically effective amount of at least one isolated immunogenic POTE polypeptide disclosed herein. In some embodiments, the method includes administering a POTE fusion protein or a nucleic acid molecule or vector encoding a POTE polypeptide. In particular embodiments, the subject has colon, ovarian, breast, prostate, lung or pancreatic cancer.

The foregoing and other objects, features, and advantages of the invention will become more apparent from the following detailed description, which proceeds with reference to the accompanying figures.

BRIEF DESCRIPTION OF THE FIGURES

(FIG. 3A) Two weeks after the second boost, splenocytes pooled from three mice were restimulated with splenocytes of naïve AAD mice pulsed with 1.0 µM of each peptide at different effector to target (E/T) ratios. Cells were cultured in anti-mouse IFN-γ antibody coated ELISPOT™ plates. After overnight culture, biotinylated anti-mouse IFN-γ antibodies were added to each well. ELISPOT™ substrates were added to develop the color and spots were counted by an ELISPOT™ reader (AID ELISPOT™ reader system). Figures show numbers of spots per million cells. (FIG. 3B) CTL cross-reactivity on each peptide. Two weeks after the second boost, pooled spleen cells from three mice were restimulated with irradiated splenocytes pulsed with 1.0 µM of peptide for 7 days. In a 4-hour $^{51}$Cr release assay, CIR.AAD cells were pulsed with 1.0 µM of peptide and labeled with $^{51}$Cr. After washing three times, target cells were mixed with different numbers of effector cells and then cultured for 4 hours before harvesting.

(FIGS. 4A and 4B) Two weeks after the second boost, splenocytes pooled from three mice were restimulated with splenocytes of naïve AAD mice pulsed with 10 nM to 1.0 µM of each peptide at different E/T ratios. Cells were cultured in anti-mouse IFN-γ antibody coated ELISPOT™ plates. After overnight culture, biotinylated anti-mouse IFN-γ antibodies were added to each well. ELISPOT™ substrates were added to develop color and spots were counted by an ELISPOT™ reader (AID ELISPOT™ reader system). Figures show numbers of spots per million cells. (FIGS. 4C and 4D) CTL cross-reactivity on each peptide. Two weeks after the second boost, pooled spleen cells from three mice were restimulated with irradiated splenocytes pulsed with 1.0 µM of peptide for 7 days. In a 4-hour $^{51}$Cr release assay, CIR.AAD cells were pulsed with 1.0 µM of peptide and labeled with $^{51}$Cr. After washing three times, target cells were mixed with different numbers of effector cells and then cultured for 4 hours before harvesting.

(FIG. 5A) Two weeks after the second boost, splenocytes pooled from three mice were restimulated with splenocytes of naïve AAD mice pulsed with 1.0 µM POTE 272 peptide at different E/T ratios. Cells were cultured in anti-mouse IFN-γ antibody coated ELISPOT™ plates. After overnight culture, biotinylated anti-mouse IFN-γ antibodies were added in each well. ELISPOT™ substrates were added to develop color and spots were counted by an ELISPOT™ reader (AID ELISPOT™ reader system). Figures show numbers of spots per million cells. (FIG. 5B) CTL reactivity on POTE 272 peptide. Two weeks after the second boost, pooled spleen cells from three mice were restimulated with irradiated splenocytes pulsed with 1.0 µM POTE 272 peptide for 7 days. In a 4-hour $^{51}$Cr release assay, CIR.AAD cells were pulsed with 1.0 µM POTE 272 peptide and labeled with $^{51}$Cr. After washing three times, target cells were mixed with different numbers of effector cells and then cultured for 4 hours before harvesting.

(FIG. 6A) Two weeks after the second boost, splenocytes pooled from three mice were restimulated with splenocytes of naïve AAD mice pulsed with 1.0 µM of each peptide at different E/T ratios. Cells were cultured in anti-mouse IFN-γ antibody coated ELISPOT™ plates. After overnight culture, biotinylated anti-mouse IFN-γ antibodies were added in each well. ELISPOT™ substrates were added to develop color and spots were counted by an ELISPOT™ reader (AID ELISPOT™ reader system). Figures show numbers of spots per million cells. (FIG. 6B) CTL cross-reactivity on POTE 323 and POTE 323-3F peptides. Two weeks after the second boost, pooled spleen cells from three mice were restimulated with irradiated splenocytes pulsed with 1.0 µM of peptide for 7 days. In a 4-hour $^{51}$Cr release assay, CIR.AAD cells were pulsed with 1.0 µM of peptide and labeled with $^{51}$Cr. After washing three times, target cells were mixed with different numbers of effector cells and then cultured for 4 hours before harvesting.

FIGS. 7A-7C are FACS plots showing HLA-A2/peptide tetramer staining and T cell receptor (TCR) repertoire determination for POTE 252- and POTE 252-9V-induced CTLs. HHD-2 mice were immunized subcutaneously with a mixture of peptide and cytokines in adjuvant. Two weeks after the second boost, pooled spleen cells from three mice were restimulated with irradiated splenocytes pulsed with 1.0 µM of peptide for 1 week. (FIG. 7A) Percentage of the HLA-A2/POTE252 tetramer-positive cells in the POTE 252- and POTE 252-9V-induced CTLs. (FIG. 7B) TCR Vβ repertoires of the tetramer$^+$CD8$^+$ T cells in POTE 252-induced CTLs. (FIG. 7C) TCR Vβ repertoires of the tetramer$^+$CD8$^+$ T cells in POTE 252-9V-induced CTLs.

(FIG. 8A) Anti-tumor cytotoxicity against a POTE-expressing human lung cancer cell line NCI-H522 induced by POTE 553-1Y, 323-3F and 252-9V. HHD-2 mice were immunized with 50 nmol of peptide in 100 µl of emulsion and restimulated for 7 days with 1000 nM peptide before being tested for ability to lyse the tumor cells. (FIG. 8B) Summary of the anti-tumor cytotoxicity in POTE-expressing and non-POTE-expressing human tumor cells. NCI-H522 is a human lung cancer line expressing both POTE and HLA-A2, whereas HTB-19 is a human mammary carcinoma that expresses POTE but not HLA-A2, and MDA-MB-231 is a human mammary carcinoma cell line expressing HLA-A2 but not POTE. Killing of only NCI-H522 shows the specificity for POTE in combination with HLA-A2.

SEQUENCE LISTING

Figure 1:
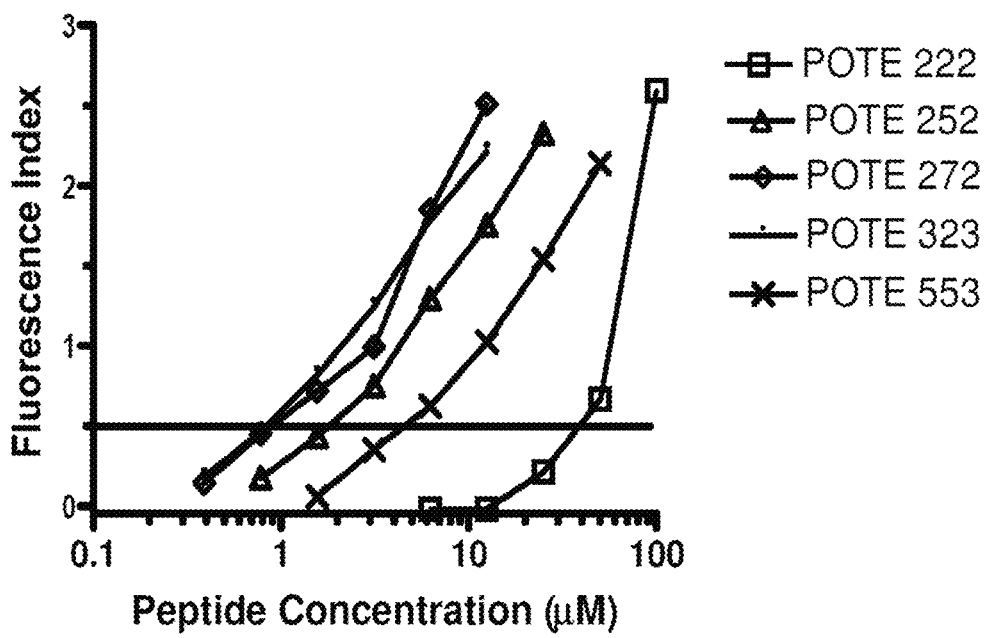
FIG. 1 is a graph showing binding affinity of POTE peptides to HLA-A2 molecules. Peptides were dissolved in DMSO in double-distilled water and different concentrations of peptides were added into the culture of TAP-deficient T2 cells. After overnight culture of the cells in medium supplemented with β2-microglobulin, cells were stained with anti-HLA-A2. HLA-A2 expression was quantified as fluorescence index (FI) according to the following formula: FI= [(mean fluorescence intensity with peptide−mean fluorescence intensity without peptide)/mean fluorescence intensity without peptide]. Background fluorescence without BB7.2 was subtracted for each individual value. To compare the different peptides, $FI_{0.5}$ (the peptide concentration that increases HLA-A2.1 expression by 50% over no peptide control background) was calculated from the titration curve for each peptide. The calculated $FI_{0.5}$ values for POTE 222, POTE 252, POTE 272, POTE 323 and POTE 553 were approximately 42.4 μM, 1.6 μM, 0.9 μM, 0.8 μM and 5.6 μM, respectively. Each assay was performed in triplicate, and data in this figure are representative of two experiments with similar results.

The amino acid sequences listed in the accompanying sequence listing are shown using standard three letter code for amino acids, as defined in 37 C.F.R. §1.822. The Sequence Listing is submitted as an ASCII text file, created on Sep. 19, 2014, 14.5 KB, which is incorporated by reference herein. In the accompanying sequence listing:

SEQ ID NO: 1 is the amino acid sequence of a human POTE protein (GenBank Accession No. NP_778146).

SEQ ID NO: 2 is the amino acid sequence of the POTE 222-230 polypeptide.

SEQ ID NO: 3 is the amino acid sequence of the POTE 252-260 polypeptide.

SEQ ID NO: 4 is the amino acid sequence of the POTE 272-280 polypeptide.

SEQ ID NO: 5 is the amino acid sequence of the POTE 323-331 polypeptide.

SEQ ID NO: 6 is the amino acid sequence of the POTE 553-561 polypeptide.

SEQ ID NOs: 7-11 are the amino acid sequences of modified POTE 252 peptides.

SEQ ID NOs: 12-15 are the amino acid sequences of modified POTE 553 peptides.

SEQ ID NOs: 16-19 are the amino acid sequences of modified POTE 323 peptides.

SEQ ID NO: 20 is the amino acid sequence of a POTE polypeptide wherein Xaa represents: Lys or Tyr at position 252; Met, Ala or Phe at position 254; Leu or Ala at position 258; Leu or Val at position 260; Leu or Tyr at position 323; Leu Ala or Phe at position 325; Val or Ala at position 329; Lys or Tyr at position 553; Ile or Leu at position 554; Leu or Phe at position 555; or Glu or Ala at position 559.

DETAILED DESCRIPTION

I. Abbreviations

BSA bovine serum albumin
CTL cytotoxic T lymphocyte
E/T effector to target
FI fluorescence intensity
FITC fluorescein isothiocyanate
HLA human leukocyte antigen
IL interleukin
IFN interferon
MHC major histocompatibility complex
PBS phosphate buffered saline
POTE protein expressed in prostate, ovary, testis and placenta
s.c. subcutaneous
TAP transporter associated with antigen processing
TCR T cell receptor

II. Terms and Methods

Unless otherwise noted, technical terms are used according to conventional usage. Definitions of common terms in molecular biology may be found in Benjamin Lewin, Genes IX, published by Jones and Bartlett Publishers, 2007 (ISBN 0763740632); Kendrew et al. (eds.), The Encyclopedia of Molecular Biology, published by Blackwell Science Inc., 1998; and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199).

Administration: The introduction of a composition into a subject by a chosen route. For example, if the chosen route is intravenous, the composition is administered by introducing the composition into a vein of the subject.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific non-limiting examples of a disease-specific antigen are an antigen whose expression correlates with, or is predictive of, tumor formation, such as prostate cancer and/or breast cancer. A disease-specific antigen can be an antigen recognized by T cells or B cells.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Cancer: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating prostate cancer or another tumor. In one embodiment, a chemotherapeutic agent is a radioactive compound. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): Oncology Pocket Guide to Chemotherapy, 2nd ed. St. Louis, Mosby-Year Book, 1995; Fischer, D. S., Knobf, M. F., Durivage, H. J. (eds): The Cancer Chemotherapy Handbook, 4th ed. St. Louis, Mosby-Year Book, 1993). Combination chemotherapy is the administration of more than one agent to treat cancer. One example is the administration of a POTE polypeptide used in combination with a radioactive or chemical compound.

Colon cancer: Cancer that forms in the tissues of the colon (the longest part of the large intestine). Colon cancer is also referred to as "colorectal cancer." Most colon cancers are adenocarcinomas (cancers that begin in cells that make line internal organs and have gland-like properties). Cancer progression is characterized by stages, or the extent of cancer in the body. Staging is usually based on the size of the tumor, whether lymph nodes contain cancer, and whether the cancer has spread from the original site to other parts of the body. Stages of colon cancer include stage I, stage II, stage III and stage IV.

Conservative variants: "Conservative" amino acid substitutions are those substitutions that do not substantially affect or decrease an activity or antigenicity of a protein, such as POTE. For example, a POTE polypeptide can include at most about 1, at most about 2, at most about 5, and most about 10, or at most about 15 conservative substitutions and specifically bind an antibody that binds the original POTE polypeptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Contacting: Placement in direct physical association. Includes both in solid and liquid form.

Epitope: An antigenic determinant. These are particular chemical groups or peptide sequences on a molecule that are antigenic, i.e. that elicit a specific immune response. An antibody specifically binds a particular antigenic epitope on a polypeptide.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

Heterologous: Originating from separate genetic sources or species. A polypeptide that is heterologous to POTE originates from a nucleic acid that does not encode POTE. In one specific, non-limiting example, the heterologous amino acid sequence includes at least a portion of β-galactosidase, maltose binding protein, albumin, or an immunoglobulin amino acid sequence. Generally, an antibody that specifically binds to a protein of interest will not specifically bind to a heterologous protein.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response (for example, a CTL response). In another embodiment, the response is a B cell response, and results in the production of specific antibodies.

Immunogenic peptide: A peptide which comprises an allele-specific motif or other sequence, such as an N-terminal repeat, such that the peptide will bind an MHC molecule and induce a CTL response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic composition: A composition comprising a POTE polypeptide that induces a measurable CTL response against cells expressing POTE polypeptide, or induces a measurable B cell response (e.g. production of antibodies) against a POTE polypeptide. It further refers to isolated nucleic acid molecules encoding a POTE polypeptide that can be used to express the POTE polypeptide (and thus be used to elicit an immune response against this polypeptide). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, POTE polypeptide, or nucleic acid encoding the polypeptide, can be readily tested for its ability to induce a CTL or B cell response by art-recognized assays. Immunogenic compositions can include adjuvants, which are well known to one of skill in the art.

Inhibiting or treating a disease: Inhibiting the full development of a disease or condition, for example, in a subject who is at risk for a disease such as a tumor (for example, a prostate tumor). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid or protein or organelle) has been substantially separated or purified away from other biological components in the cell of the organism in which the component naturally occurs, such as other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Linker: One or more nucleotides or amino acids that serve as a spacer between two molecules, such as between two nucleic acid molecules or two peptides (such as in a fusion protein).

Lung cancer: Cancer that forms in tissues of the lung, usually in the cells lining air passages. The two primary types of lung cancer are small cell lung carcinoma and non-small cell lung carcinoma (NSCLC). NSCLC includes, for example, squamous cell lung carcinoma, adenocarcinoma and large cell lung carcinoma.

Mammal: This term includes both human and non-human mammals. Similarly, the term "subject" includes both human and veterinary subjects.

Major histocompatibility complex (MHC): Generic designation meant to encompass the histocompatibility antigen systems described in different species, including the human leukocyte antigens ("HLA"). The term "motif" or "epitope" refers to the pattern of residues in a peptide of defined length, usually about 8 to about 11 amino acids, which is recognized by a particular MHC allele. The peptide motifs or epitopes are typically different for each MHC allele and differ in the pattern of the highly conserved residues and negative binding residues.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary. Most ovarian cancers are either ovarian epithelial carcinomas (cancer that begins in the cells on the surface of the ovary) or malignant germ cell tumors (cancer that begins in egg cells), but may also arise from tissue of the Fallopian tube.

Pancreatic cancer: A malignant neoplasm of the pancreas. Pancreatic cancer is also referred to as exocrine cancer. About 95% of exocrine pancreatic cancers are adenocarcinomas. The remaining 5% include adenosquamous carcinomas, signet ring cell carcinomas, hepatoid carcinomas, colloid carcinomas, undifferentiated carcinomas, and undifferentiated carcinomas with osteoclast-like giant cells. Exocrine pancreatic cancers are far more common than endocrine pancreatic cancers (also known as islet cell carcinomas), which make up about 1% of total cases.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide or peptide: Any chain of amino acids regardless of length or post-translational modification (such as glycosylation or phosphorylation). In some embodiments, a polypeptide is between 3 and 600 amino acids in length, including 3 to 100, 3 to 50, 3 to 20, 3 to 10 or 8 to 10 amino acids in length. In particular examples, a POTE polypeptide is 8, 9 or 10 amino acids in length.

A "POTE polypeptide" or "POTE peptide" is a series of contiguous amino acid residues from a POTE protein. In one example, with respect to immunogenic compositions comprising a POTE peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a MHC class I molecule, to activate cytotoxic T lymphocytes against cells expressing wild-type POTE protein. Induction of CTLs using synthetic peptides and CTL cytotoxicity assays are taught in, e.g., U.S. Pat. No. 5,662,907.

A "residue" refers to an amino acid or amino acid mimetic incorporated in a polypeptide by an amide bond or amide bond mimetic.

Polypeptide modifications: POTE polypeptides include synthetic embodiments of peptides described herein. In addition, analogs (non-peptide organic molecules), derivatives (chemically functionalized peptide molecules obtained starting with the disclosed peptide sequences) and variants (homologs or paralogs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the POTE peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a POTE polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Polypeptide modifications also include amino acid substitutions, such as the alter binding affinity of the polypeptide to MHC molecules. Exemplary amino acid substitutions for altering MHC binding affinity are disclosed herein and have been described in the art (see, for example, Berzofsky et al., *Nat. Rev. Immunol.* 1(3):209-219, 2001).

POTE polypeptides: A family of polypeptides that is expressed in prostate, ovary, testis, and placenta, as well as in prostate cancer (Bera et al., *Proc. Natl. Acad. Sci. U.S.A.* 99:16975-16980, 2002). The POTE-21 gene has 11 exons and spans a 32 kb region of human chromosome 21. The 1.8 kb transcript of POTE-21 encodes a protein of molecular weight of about 66 kDa. This polypeptide is designated "POTE-21" or "POTE" in this disclosure. In one embodiment, POTE is 584 amino acids in length, is about 66.4 kDa, and is encoded by human chromosome 21. This POTE protein (POTE-21) has seven ankyrin repeats and three N-terminal repeats. An exemplary amino acid sequence of POTE-21 is provided as SEQ ID NO: 1. In some cases, "POTE" as used herein refers to POTE-21 but can also refer to any POTE paralog.

Amino acid sequence analysis of additional POTE polypeptides (encoded by POTE paralogs) revealed that they have ankyrin repeats as well as spectrin motifs at the carboxy terminus of the protein. Ankyrin repeats are tandemly repeated modules of about 33 amino acids each, that are present in functionally diverse proteins and mediate protein-protein interactions (Michel, *EMBO J.* 20:6180-6190, 2001). Spectrins, on the other hand, are major constituents of the cytoskeleton that are anchored to the plasma membrane by means of protein complexes that include ankyrins (Djinovic-Carugo et al., *FEBS Lett* 513:119-123, 2002).

A "nucleic acid paralog" is a related gene, and a "polypeptide paralog" is a protein encoded by such a related gene. Several "paralogs" of POTE are encoded by chromosomes 2, 8, 13, 14, 14, 18, 21, and 22 have been identified. The paralogs were identified by aligning a cDNA encoding POTE (as encoded by chromosome 21) with the human genome. At least nine significant matches with this sequence were identified on chromosomes 22, 15, 2, 14, and 8 (see Bera et al., *Proc. Natl. Acad. Sci* 99:16975-16980, 2002). Exemplary POTE nucleic acid paralogs have been identified at the following locations:

| Chromosome | Strand | Start | End | Score | cDNA Start | cDNA End | Identity |
|---|---|---|---|---|---|---|---|
| 21 | + | 11645620 | 11677028 | 1808 | 0 | 1826 | 99.8 |
| 15 | + | 1815046 | 18746092 | 1738 | 0 | 1826 | 98.1 |
| 2 | + | 140937343 | 141259911 | 1487 | 0 | 1779 | 92.7 |
| 14 | − | 17309857 | 17339582 | 1348 | 0 | 1585 | 93.2 |
| 2A | + | 141927000 | 141961449 | 1346 | 0 | 1743 | 92.5 |
| 2B | − | 124217411 | 124260895 | 1344 | 0 | 1585 | 93.0 |
| 8 | − | 43962699 | 44033444 | 1068 | 10 | 1825 | 89.3 |
| 22 | − | 13206523 | 13232594 | 976 | 571 | 1743 | 92.7 |
| 2C | − | 140822569 | 140835195 | 928 | 0 | 1188 | 93.8 |
| 8 | + | 47053750 | 47094566 | 433 | 1107 | 1825 | 89.1 |

The additional POTE polypeptides encoded by these nucleic acid sequences are designated "POTE paralogs" or "POTE polypeptides," and are designated POTE-2α, -β, etc. based on the human chromosome that encodes the polypeptide. Specific amino acid sequences of exemplary POTE paralogs are publically available and have been previously disclosed (see, for example, PCT Publication No. WO 2005/080436).

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter). Promoters produced by recombinant DNA or synthetic techniques can also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Prostate Cancer: A malignant tumor, generally of glandular origin, of the prostate. Prostate cancers include adenocarcinomas and small cell carcinomas. Many prostate cancers express prostate specific antigen (PSA).

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. A substantially purified protein is at least 60%, 70%, 80%, 90%, 95% or 98% pure. Thus, in one specific, non-limiting example, a purified protein is 90% free of other proteins or cellular components. The POTE polypeptides disclosed herein can be purified by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a POTE polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a POTE polypeptide are typically characterized by possession of at least about 75%, for example at least about 80%, 90%, 95%, 96%, 97%, 98% or 99% sequence identity counted over the full length alignment with the amino acid sequence of POTE or a POTE paralog using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals.

T cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, $CD8^+$ T cells are cytotoxic T lymphocytes. In another embodiment, a $CD8^+$ T cell is a suppressor T cell.

Therapeutically effective amount: A quantity of a specified agent sufficient to achieve a desired effect in a subject, cell or culture being treated with that agent. In the context of the present disclosure, a therapeutically effective amount of a POTE polypeptide is an amount of POTE polypeptide that causes induction of an immune response, as measured by clinical response (for example increase in a population of immune cells, production of antibody that specifically binds the polypeptide, or measurable reduction of tumor burden). In one embodiment, a therapeutically effective amount of a POTE polypeptide is an amount used to generate an immune response, or to treat cancer (such as colon, ovarian, breast, prostate, lung or pancreatic cancer) in a subject. In another embodiment, a therapeutically effective amount of a POTE polypeptide is an amount sufficient for inducing a tumor-specific CTL response.

Tumor or cancer antigen: An antigen that can stimulate tumor-specific T-cell immune responses.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank accession numbers are incorporated herein as they appear in the NCBI database as of Mar. 12, 2010. In case of conflict, the present specification, including explanations of terms, will control. In addition, the materials, methods, and examples are illustrative only and not intended to be limiting.

III. Introduction

Identification of CD8$^+$ T cell epitopes that can induce T cells to kill tumor cells is a fundamental step for development of a peptide cancer vaccine. POTE protein has been previously identified as a cancer antigen expressed in a wide variety of human cancers, including colon, lung, breast, ovary and pancreas (Ruppert et al., Cell 74:929-937, 1993). Because only limited normal tissues express POTE antigen, POTE is a potential target protein for cancer immunotherapy for a variety of cancers.

In the studies disclosed herein, HLA-A2.1-restricted CTL epitopes in the POTE protein were determined, and enhanced epitopes were designed by amino acid substitutions. Five 9-mer peptides were first selected and their binding affinity to HLA-A2 molecules was measured by the T2 binding assay. POTE 272-280 and POTE 553-561 showed the strongest HLA-A2 binding affinity. POTE 252-260 and POTE 323-331 were intermediate binders. After epitope enhancement, epitopes with amino acid substitutions conferring higher affinity for HLA-A2, POTE 252-9V (valine at position 9), POTE 552-1Y (tyrosine at position 1) and POTE 323-3F (phenylalanine at position 3) induced CTL responses cross-reactive with wild-type antigens, POTE 252-9V most strongly, but POTE 323-3F had the greatest increase in immunogenicity compared to wild type. Based on the binding data, these modified epitopes have the greatest potential to serve as vaccine targets for cancer patients. A combination of POTE 252-9V, POTE 553-1Y and POTE 323-3F epitopes is one example of an attractive vaccine strategy to overcome tolerance induced by tumors. As nearly half of the American population is HLA-A2$^+$, the POTE peptides described herein can serve as effective cancer vaccines for a large group of individuals. In some embodiments of the disclosed methods, an HLA-A2$^+$ subject is selected for vaccination with the POTE peptide(s).

IV. Immunogenic POTE Polypeptides

POTE is a newly found tumor antigen expressed in breast, prostate, colon, lung, ovarian and pancreatic cancer. Because POTE expression is limited in normal tissues, POTE is a potential target protein for cancer immunotherapy for a variety of cancers.

Disclosed herein are immunogenic POTE polypeptides, including modified POTE polypeptides, capable of binding MHC class I molecules, such as HLA-A2, which is expressed by nearly 50% of the American population. The amino acid sequences of the disclosed POTE polypeptides include CD8$^+$ T cell epitopes and are thus capable of inducing an immune response in a subject and serve as targets for the killing of tumor cells that express POTE. The disclosed POTE polypeptides, both modified and unmodified POTE polypeptides, are proposed as vaccines for the treatment of cancer, including breast, prostate, colon, lung, ovarian and pancreatic cancer.

Provided herein are isolated polypeptides comprising no more than 10 consecutive amino acids of the amino acid sequence of human POTE. In some embodiments, human POTE comprises the sequence set forth as: MVAEVCSMPTASTVKKPFDLRSKMGKWCHHRFPCCRGSGKSNMGTSGDHDD SFMKMLRSKMGKCCRHCFPCCRGSGTSNVGTSGDHENSFMKMLRSKMG KWC CHCFPCCRGSGKSNVGAWGDYDHSAFMEPRYHIRREDLDKLHRAAWWGKVP RKDLIVMLRDTDMNKRDKEKRTALHLASANGNSEVVQLLLDRRCQLNVLDNK KRTALIKAIQCQEDECVLMLLEHGADRNIPDEYGNTA LHYAIYNEDX$_1$LX$_2$AKA X$_3$LX$_4$YGADIESKNKCGLTPLLLGVHEQKQQVVKFLI KKKANLNVLDRYGRTAL ILAVCCGSASIVNX$_5$LX$_6$EQNX$_7$DVSSQDLSGQTAREY AVSSHHHVICELLSDYK EKQMLKISSENSNPEQDLKLTSEEESQRLKVSENSQPEKMSQEPEINKDCDREVE EEIKKHGSNPVGLPENLTNGASAGNGDDGLIPQRRSRKPENQQFPDTENEEYHS DEQNDTRKQLSEEQNTGISQDEILTNKQKQIEVAEQKMNSELSLSHKKEEDLLR ENSVLQEEIAMLRLELDETKHQNQLRENX$_8$X$_9$X$_{10}$EE IX$_{11}$SVKEKTDKLLRAMQL NEEALTKTNI (SEQ ID NO: 20), wherein X$_1$ is K or Y; X$_2$ is M, A or F; X$_3$ is L or A; X$_4$ is L or V; X$_5$ is L or Y; X$_6$ is L, A or F; X$_7$ is V, or A; X$_8$ is K or Y; X$_9$ is I or L; X$_{10}$ is L or F; and X$_{11}$ is E or A.

In some embodiments, the POTE polypeptide comprises one of (a) amino acids 222-230; (b) amino acids 252-260; (c) amino acids 272-280; (d) amino acids 323-331; or (e) amino acids 553-561 of SEQ ID NO: 20. However, in some embodiments, the polypeptide does not comprise the amino acid sequence KLMAKALLL (SEQ ID NO: 3), which is the unmodified amino acid sequence of residues 252-260 of human POTE-21 (SEQ ID NO: 1).

The POTE polypeptides provided herein are 8, 9 or 10 amino acids in length. In particular embodiments, the POTE polypeptides comprise 9 amino acids in length. Thus, in some examples, the POTE polypeptides comprise 9 consecutive amino acids of SEQ ID NO: 20 or SEQ ID NO: 1.

In some embodiments, the isolated POTE polypeptide comprises amino acids 222-230 of SEQ ID NO: 20. In some examples, a modified POTE polypeptide is provided which comprises amino acids 222-230 of SEQ ID NO: 20 with one or more amino acid substitutions to alter binding affinity to MHC class I. In some examples, the POTE polypeptide is an unmodified polypeptide, which polypeptide is set forth herein as SEQ ID NO: 2.

In other embodiments, the isolated POTE polypeptide comprises amino acids 252-260 of SEQ ID NO: 20. In some examples, the POTE polypeptide is an unmodified POTE polypeptide comprising amino acids 252-260 of human POTE, which polypeptide is set forth herein as SEQ ID NO: 3. In some examples, the POTE polypeptide comprises amino acids 252-260 of SEQ ID NO: 20, wherein $X_1$ is Y; $X_2$ is A; $X_2$ is F; $X_3$ is A; and/or $X_4$ is V. Thus, in some examples, the POTE polypeptide comprises or consists of the amino acid sequence of SEQ ID NO: 7 (POTE 252-1Y), SEQ ID NO: 8 (POTE 252-3A), SEQ ID NO: 9 (POTE 252-3A), SEQ ID NO: 10 (POTE 252-7A) or SEQ ID NO: 11 (POTE 252-9V).

In other embodiments, the isolated POTE polypeptide comprises amino acids 272-280 of SEQ ID NO: 20. In some examples, a modified POTE polypeptide is provided which comprises amino acids 272-280 of SEQ ID NO: 20 with one or more amino acid substitutions to alter binding affinity to MHC class I. In some examples, the POTE polypeptide is an unmodified polypeptide, which polypeptide is set forth herein as SEQ ID NO: 4.

In other embodiments, the isolated POTE polypeptide comprises amino acids 323-331 of SEQ ID NO: 20. In some examples, the POTE polypeptide is an unmodified POTE polypeptide comprising amino acids 323-331 of human POTE, which polypeptide is set forth herein as SEQ ID NO: 5. In some examples, the POTE polypeptide comprises amino acids 323-331 of SEQ ID NO: 20, wherein $X_5$ is Y; $X_6$ is A; $X_6$ is F; and/or $X_7$ is A. Thus, in some examples, the POTE polypeptide comprises or consists of the amino acid sequence of SEQ ID NO: 16 (POTE 323-1Y), SEQ ID NO: 17 (POTE 323-3A), SEQ ID NO: 18 (POTE 323-3F) or SEQ ID NO: 19 (POTE 323-7A).

In other embodiments, the isolated POTE polypeptide comprises amino acids 553-561 of SEQ ID NO: 20. In some examples, the POTE polypeptide is an unmodified POTE polypeptide comprising amino acids 553-561, which polypeptide is set forth herein as SEQ ID NO: 6. In some examples, the POTE polypeptide comprises amino acids 553-561 of SEQ ID NO: 20, wherein $X_8$ is Y; $X_9$ is L; $X_{10}$ is F; and/or $X_{11}$ is A. Thus, in some examples, the POTE polypeptide comprises or consists of the amino acid sequence of SEQ ID NO: 12 (POTE 553-1Y), SEQ ID NO: 13 (POTE 553-2L), SEQ ID NO: 14 (POTE 553-3F) or SEQ ID NO: 15 (POTE 553-7A).

It is believed that the presentation of peptides by MHC class I molecules involves binding to the cleft in an MHC class I molecule through the anchor residues of the peptide and ultimate presentation on the cell surface. Depending upon the particular anchor residues, among other things, certain peptides can bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC class I molecules present epitopes from endogenous proteins for presentation to CTL cells. HLA-A, HLA-B and HLA-C molecules bind peptides of about 8 to 10 amino acids in length that have particular anchoring residues. The anchoring residues recognized by an HLA class I molecule depend upon the particular allelic form of the HLA molecule. A $CD8^+$ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the polypeptides that are disclosed bind and are presented by HLA-A2.

In specific, non-limiting examples, an immunogenic POTE polypeptide includes one of the following amino acid sequences, or a sequence that is at least 88% identical to one of the following amino acid sequences (for example, having a single conservative amino acid substitution):

POTE 222-230
VLMLLEHGA
SEQ ID NO: 2

POTE 252-260
KLMAKALLL
SEQ ID NO: 3

POTE 252-1Y
YLMAKALLL
SEQ ID NO: 7

POTE 252-3A
KLAAKALLL
SEQ ID NO: 8

POTE 252-3F
KLFAKALLL
SEQ ID NO:9

POTE 252-7A
KLMAKAALL
SEQ ID NO: 10

POTE 252-9V
KLMAKALLV
SEQ ID NO: 11

POTE 272-280
GLTPLLLGV
SEQ ID NO: 4

POTE 553-561
KILEEIESV
SEQ ID NO: 6

POTE 553-1Y
YILEEIESV
SEQ ID NO: 12

POTE 553-2L
KLLEEIESV
SEQ ID NO: 13

POTE 553-3F
KIFEEIESV
SEQ ID NO: 14

POTE-553-7A
KILEEIASV
SEQ ID NO: 15

-continued

POTE 323-331
SEQ ID NO: 5
LLLEQNVDV

POTE 323-1Y
SEQ ID NO: 16
YLLEQNVDV

POTE 323-3A
SEQ ID NO: 17
LLAEQNVDV

POTE 323-3F
SEQ ID NO: 18
LLFEQNVDV

POTE 323-7A
SEQ ID NO: 19
LLLEQNADV

Also provided herein are fusion proteins including a POTE polypeptide and a heterologous amino acid sequence. Any heterologous amino acid sequence is contemplated, including tags or labels, or proteins that enhance the immune response elicited by the POTE polypeptide. In several specific non-limiting examples, the immunogenic POTE peptide is a fusion polypeptide in which the heterologous amino acid sequence includes six sequential histidine residues (a His tag), a β-galactosidase amino acid sequence, or an immunoglobulin amino acid sequence. The polypeptide can also be covalently linked to a carrier.

A POTE polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-5197, 1999; Lee et al., *J. Immunol.* 116:1711-1718, 1976; Dintzis et al., *PNAS* 73:3671-3675, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms, such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide).

The polypeptide can optionally include repetitions of any one of SEQ ID NOs: 2-19. In one specific, non-limiting example, the polypeptide includes 2, 3, 4, 5, or up to ten repetitions of one of the sequences set forth as SEQ ID NOs: 2-19. A linker sequence can optionally be included between the repetitions.

The immunogenic POTE polypeptides disclosed herein can also be chemically synthesized by standard methods, or can be produced recombinantly. An exemplary process for polypeptide production is described in Lu et al., *Federation of European Biochemical Societies Letters*. 429:31-35, 1998.

Immunogenic POTE polypeptides can also be isolated by methods including preparative chromatography and immunological separations.

Nucleic acid molecules encoding the immunogenic POTE polypeptides disclosed herein are also provided. These polynucleotides include DNA, cDNA and RNA sequences which encode the polypeptide of interest.

A nucleic acid molecule encoding an immunogenic POTE polypeptide can be cloned or amplified by in vitro methods, such as the polymerase chain reaction (PCR), the ligase chain reaction (LCR), the transcription-based amplification system (TAS), the self-sustained sequence replication system (3SR) or the Qβ replicase amplification system (QB). For example, a polynucleotide encoding the protein can be isolated by PCR of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). POTE-encoding nucleic acid molecules also can be isolated by screening genomic or cDNA libraries with probes selected from the sequences of the desired polynucleotide under stringent hybridization conditions.

The nucleic acid molecules encoding an immunogenic POTE polypeptide include nucleic acid molecules encoding a POTE polypeptide that are incorporated into a vector, such as an autonomously replicating plasmid or virus, or that exist as a separate molecule (e.g., a cDNA) independent of other sequences. The nucleotides of the disclosure can be ribonucleotides, deoxyribonucleotides, or modified forms of either nucleotide. The term includes single and double stranded forms of DNA.

DNA sequences encoding an immunogenic POTE polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

A nucleic acid sequence encoding an immunogenic POTE polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The nucleic acid sequences encoding an immunogenic POTE polypeptide can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an immunogenic POTE polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Further provided are compositions comprising one or more of the immunogenic POTE polypeptides disclosed herein. The provided compositions further include compositions comprising a POTE polypeptide fusion protein disclosed herein. Also provided are compositions comprising an isolated nucleic acid molecule encoding an immunogenic POTE polypeptide. In some embodiments, the isolated nucleic acid molecule is a vector encoding a POTE polypeptide.

In some embodiments disclosed herein, the compositions further comprise a pharmaceutically acceptable carrier. In some examples, the compositions provided herein further include an adjuvant.

V. POTE Polypeptide Compositions and Methods of Use

An immunogenic POTE polypeptide as disclosed herein can be administered to a subject in order to generate an immune response. Thus, provided herein is a method of eliciting an immune response in a subject by selecting a subject in need of treatment, and administering to the subject a therapeutically effective amount of at least one isolated immunogenic POTE polypeptide disclosed herein, or administering a POTE polypeptide fusion protein, thereby eliciting an immune response in the subject. In some embodiments, the immune response comprises an anti-tumor CTL response.

In some embodiments, an immunogenic POTE polypeptide is administered that includes one of the following amino acid sequences, or a sequence that is at least 88% identical to one of the following amino acid sequences (for example, having a single conservative amino acid substitution):

```
POTE 222-230
                                SEQ ID NO: 2
VLMLLEHGA

POTE 252-260
                                SEQ ID NO: 3
KLMAKALLL

POTE 252-1Y
                                SEQ ID NO: 7
YLMAKALLL

POTE 252-3A
                                SEQ ID NO: 8
KLAAKALLL
```

```
POTE 252-3F
                                SEQ ID NO: 9
KLFAKALLL

POTE 252-7A
                                SEQ ID NO: 10
KLMAKAALL

POTE 252-9V
                                SEQ ID NO: 11
KLMAKALLV

POTE 272-280
                                SEQ ID NO: 4
GLTPLLLGV

POTE 553-561
                                SEQ ID NO: 6
KILEEIESV

POTE 553-1Y
                                SEQ ID NO: 12
YILEEIESV

POTE 553-2L
                                SEQ ID NO: 13
KLLEEIESV

POTE 553-3F
                                SEQ ID NO: 14
KIFEEIESV

POTE-553-7A
                                SEQ ID NO: 15
KILEEIASV

POTE 323-331
                                SEQ ID NO: 5
LLLEQNVDV

POTE 323-1Y
                                SEQ ID NO: 16
YLLEQNVDV

POTE 323-3A
                                SEQ ID NO: 17
LLAEQNVDV

POTE 323-3F
                                SEQ ID NO: 18
LLFEQNVDV

POTE 323-7A
                                SEQ ID NO: 19
LLLEQNADV
```

In some embodiments of the method, the POTE polypeptide administered does not comprise the amino acid sequence of SEQ ID NO: 3.

In one specific, non-limiting example, the immunogenic POTE polypeptide comprises or consists of an amino acid sequence selected from SEQ ID NO: 11 (POTE 252-9V), SEQ ID NO: 12 (POTE 553-1Y) and SEQ ID NO: 18 (POTE 323-3F).

One or more of the immunogenic POTE polypeptides disclosed herein can be administered to a subject to treat a cancer that expresses POTE, such as colon, ovarian, breast, prostate, lung or pancreatic cancer. Thus, for example, one, two, three, four or five of the immunogenic POTE polypeptides disclosed herein can be administered to a subject. In some examples, two or three immunogenic POTE polypeptides are administered to the subject in need of treatment. In particular examples when the subject is administered two or three immunogenic POTE polypeptides, the polypeptides each comprise a different sequence selected from the group consisting of SEQ ID NO: 11 (POTE 252-9V), SEQ ID NO: 12 (POTE 553-1Y) and SEQ ID NO: 18 (POTE 323-3F).

In some embodiments, the step of selecting a subject in need of treatment includes selecting a subject that has been diagnosed with colon, ovarian, breast, prostate, lung or pancreatic cancer. In some embodiments, selecting a subject in need of treatment includes selecting a subject with cancerous cells (or a tumor) that expresses POTE. Cancers that express POTE include, for example, colon, ovarian, breast, prostate, lung or pancreatic cancer. In some cases, the subject has undergone or will undergo other cancer-specific treatments, including surgery, chemotherapy or radiation therapy. In some embodiments of the disclosed methods, an HLA-A2+ subject is selected for vaccination with the POTE peptide(s).

In exemplary applications, compositions are administered to a patient suffering from a disease, such as colon, ovarian, breast, prostate, lung or pancreatic cancer, in an amount sufficient to raise an immune response to POTE-expressing cells. Administration induces a sufficient immune response to slow the proliferation of such cells or to inhibit their growth, or to reduce a sign or a symptom of the tumor. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

An immunogenic POTE polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts can also be used as adjuvants to produce an immune response.

In one specific, non-limiting example, an immunogenic POTE polypeptide is administered in a manner to direct the immune response to a cellular response (that is, a CTL response), rather than a humoral (antibody) response. A number of means for inducing cellular responses, both in vitro and in vivo, are known. Lipids have been identified as agents capable of assisting in priming CTLs in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic POTE polypeptide, a MHC class II-restricted T-helper epitope is added to the immunogenic POTE polypeptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including an immunogenic POTE polypeptide is thus provided. In one embodiment, the immunogenic POTE polypeptide is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770. A stabilizing detergent is any detergent that allows the components of the emulsion to remain as a stable emulsion. Such detergents include polysorbate, 80 (TWEEN) (Sorbitan-mono-9-octadecenoate-poly (oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion (i.e., to provide a vehicle for the desired antigen) and preferably has a melting temperature of less than 65° C. such that an emulsion is formed either at room temperature (about 20° C. to 25° C.), or once the temperature of the emulsion is brought down to room temperature. Examples of such oils include squalene, squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name PROVAX® (Biogen Idec, San Diego, Calif.). An adjuvant can also be an immunostimulatory nucleic acid, such as a nucleic acid including a CpG motif.

In another embodiment, a pharmaceutical composition includes a nucleic acid encoding an immunogenic POTE polypeptide (also referred to herein as an immunogenic POTE polynucleotide). A therapeutically effective amount of the immunogenic POTE polynucleotide can be administered to a subject in order to generate an immune response. In one specific, non-limiting example, a therapeutically effective amount of the immunogenic POTE polynucleotide is administered to a subject to treat colon, ovarian, breast, prostate, lung or pancreatic cancer.

One approach to administration of nucleic acids is direct immunization with plasmid DNA, such as with a mammalian expression plasmid. As described above, the nucleotide sequence encoding an immunogenic POTE polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as encapsulated in ISCOMS™ have been found to produce MHC class I mediated CTL responses (Takahashi et al., *Nature* 344:873, 1990).

In another approach to using nucleic acids for immunization, an immunogenic POTE polypeptide can be expressed by attenuated viral hosts or vectors or bacterial vectors. Recombinant vaccinia virus, adeno-associated virus, herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding an immunogenic POTE polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration would include about 0.1 µg to 10 mg of immunogenic POTE polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Sciences*, 19$^{th}$ Ed., Mack Publishing Company, Easton, Pa., 1995.

The compositions can be administered for therapeutic treatments. In therapeutic applications, a therapeutically effective amount of the composition is administered to a subject suffering from a disease, such as colon, ovarian, breast, prostate, lung or pancreatic cancer. Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

In another method, antigen presenting cells (APCs), such as dendritic cells, are pulsed or co-incubated with peptides comprising an immunogenic POTE polypeptide in vitro. In one specific, non-limiting example, the antigen presenting cells can be autologous cells. A therapeutically effective amount of the antigen presenting cells can then be administered to a subject.

The immunogenic POTE polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 μg to about 1,000 μg, or about 1 to about 100 μg of a selected immunogenic POTE polypeptide. The immunogenic POTE polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic POTE polypeptide. These dendritic cells are then administered alone to a subject with a tumor that expresses POTE, such as a colon, ovarian, breast, prostate, lung or pancreatic cancer. In another embodiment, the mature dendritic cells are administered in conjunction with a chemotherapeutic agent.

Alternatively, the APCs are used to sensitize CD8$^+$ cells, such as tumor infiltrating lymphocytes (TILs) from prostate or breast tumors (or another type of cancer) or peripheral blood lymphocytes (PBLs). The TILs or PBLs can be from the same subject (autologous) that is to be treated. Alternatively, the TILs or PBLs can be heterologous. However, they should at least be MHC class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as POTE (e.g. SEQ ID NO: 1).

The cells can be administered to a subject to inhibit the growth of cells of POTE expressing tumors. In these applications, a therapeutically effective amount of activated antigen presenting cells, or activated lymphocytes, are administered to a subject suffering from a disease, in an amount sufficient to raise an immune response to POTE-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as IL-2, IL-3, IL-6, IL-10, IL-12, IL-15, GM-CSF, or interferons, or a combination of two or more cytokines, such as 2, 3, 4, 5, 6, 7 or more cytokines.

In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocyin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

The following examples are provided to illustrate certain particular features and/or embodiments. These examples should not be construed to limit the disclosure to the particular features or embodiments described.

EXAMPLE

Example 1

Materials and Methods

This example describes the materials and experimental procedures used for the studies described in Example 2 and Example 3.

Animals

AAD mice (Newberg et al., *J Immunol* 156(7):2473-2480, 1996) expressing a chimeric HLA-A2.1 transgene with the al and cc2 domains from HLA-A2.1 and the cc3 domain from H-2D$^d$ (to allow binding to mouse CD8) on a $C_{57}BL/6$ background, were used in these experiments. Parts of the experiments were repeated in HHD-2 mice, which express chimeric human HLA-A2.1 with the covalent human β2m, without any murine class I molecule. Mice were bred and housed in appropriate animal care facilities. All procedures with animals were conducted in accordance with the institutional approved protocols.

Peptides

Peptides in this study were synthesized on a Model Symphony Peptide Synthesizer (Perkin-Elmer, Boston, Mass.)

using conventional fluorenylmethoxycarbonyl (f-MOC) chemistry and cleaved from the resin by trifluoroacetic acid. The purity and molar concentration were analyzed by reverse phase high-performance liquid chromatography on a $C_{18}$ column using a gradient of 0.1% trifluoroacetic acid in water and 0.1% trifluoroacetic acid in acetonitrile and further purified by preparative reverse-phase high-performance liquid chromatography using a similar gradient.

Cell Lines

The T2 cell line is deficient for TAP1 and TAP2 transporter proteins and expresses low levels of HLA-A2 (Nijman et al., Eur J Immunol 23:1215-1219, 1993). The $C_1R.AAD$ cell line is derived from the human B lymphoblastoid cell line $HMYC_1R$ transfected with the HLA chimeric molecule containing al and cc2 domains from human HLA-A2.1 and cc3 from mouse $H-2D^d$ as previously described (Newberg et al., J Immunol 156(7):2473-2480, 1996). The $C_1R.A2.1$ cell line is also derived from $HMYC_1R$ transfected with HLA-A2.1. $C_1R.AAD$ and $C_1R.A2.1$ cells were maintained in complete medium consisting of 10% FCS-RPMI, 1 mM sodium pyruvate, nonessential amino acids (Biofluid, Rockville, Md.), 4 mM glutamine, 100 U/ml penicillin, 100 µg/ml streptomycin, and 50 µM 2-ME. NCI-H522 (POTE+/HLA-A2) was maintained in the complete medium. HTB-19 (POTE+/HLA-A1) was maintained in Eagle's minimum essential medium (EMEM) with 5% FCS. MDA-MB-231 (POTE-/HLA-A2) was maintained in 10% FCS-DMEM.

T2 Binding Assay

Peptide binding capacity to the HLA-A2 molecule was measured by using the T2 cell line according to a protocol described previously (Peters et al., Bioinformatics 19(14): 1765-1772, 2003). T2 cells ($3 \times 10^5$ cells/well) were incubated overnight in 96-well plates with culture medium (1:1 mixture of RPMI 1640/Eagle-Hank's amino acid containing 2.5% fetal bovine serum, 100 U/ml penicillin, and 100 µg/ml streptomycin) with 10 µg/ml β2-microglobulin (Sigma) and different titrated concentrations of peptides (starting from 100 µM with 2-fold serial dilution) as shown in the figures to determine the concentration giving a 50% increasing in binding. Cells were washed once with cold HBSS containing 0.1% BSA and incubated for 30 minutes at 4° C. with anti-HLA-A2.1 BB7.2 monoclonal antibody (1:40 dilution from hybridoma supernatant). After washing, cells were stained with FITC-labeled goat anti-mouse immunoglobulin (BD, San Jose, Calif.), and the level of HLA expression was measured by flow cytometry. HLA-A2 expression was quantified as fluorescence index (FI) according to the following formula: FI=[(geometric mean fluorescence intensity with peptide-geometric mean fluorescence intensity without peptide)/ geometric mean fluorescence intensity without peptide]. Background fluorescence without BB7.2 was subtracted for each individual value. To compare the different peptides, $FI_{0.5}$, the peptide concentration that increases HLA-A2.1 expression by 50% over no peptide control background, was calculated from the titration curve for each peptide.

Immunizations

AAD or HHD-2 mice were immunized subcutaneously (s.c.) in the base of the tail with 100 µl of an emulsion containing 1:1 incomplete Freund's adjuvant (Sigma) and PBS with peptides and cytokines (50 nmol of CTL epitope, 50 nmol of hepatitis B virus core 128-140 helper epitope, 5 µg of mouse interleukin-12, and 5 µg of mouse granulocyte macrophage colony-stimulating factor). Cytokines were purchased from Peprotech (Rocky Hill, N.J.). Mice were boosted 2 weeks later, and the spleens were removed 2 weeks after the boost. For all experiments, groups of three mice were used.

Interferon-γ ELISPOT™ Assay

The numbers of IFN-γ secreting cells were determined by an ELISPOT™ kit (Mouse IFN-gamma ELISPOT™ SixPak; R&D, Minneapolis, Mass.) or by a set of anti-mouse IFN-γ coating (AN18) and detecting (R4-6A2) monoclonal antibodies (Mabtech) according to the manufacturer's instructions. Two weeks after the last immunization, spleen cells were plated on antibody-coated plates at 200,000, 100,000 and 50,000 cells/well and stimulated with 200,000 peptide-pulsed naïve spleen cells/well with the indicated concentration of peptides for 2 hours. After incubation overnight at 37° C., the plates were washed and detecting antibody was added. An ELISPOT™ blue color module (R&D) was used for color development. The spots were read by an ELISPOT™ reader (AID). All samples were analyzed in triplicate.

In Vitro Stimulation and Cytotoxicity Assay

Splenocytes from the immunized mice were re-stimulated with peptide-loaded splenocytes (1 µM, or 10 nM). On day 1 and day 5, rat T STIM™ (BD Bioscience) was added as a source of IL-2. One week later, CTL activity was measured by using a 4-hour $^{51}Cr$ releasing assay. Target cells ($10^6$) were pulsed with peptides in 200 µl of complete T cell medium and 150 µCi of $^{51}Cr$ for 2 hours, washed three times, and added at 3000 cells/well to the 96-well round-bottom plates with different effector to target (E/T) ratios. The percentage of specific $^{51}Cr$ release is calculated as 100× [(experimental release-spontaneous release)/(maximum release-spontaneous release)]. Spontaneous release is determined from target cells incubated without effector cells, and maximum release is determined in the presence of 5% triton-X. $C_1R.AAD$ or $C_1R.A2.1$ cell lines were used as targets. These do not express any other MHC molecule, either class I or class II, besides HLA-A2, so they are not subject to concerns about allo- or xenoreactivity. Human cancer cells were pre-incubated with 1000 ng/ml human IFN-γ for 72 hours prior to the assay (Oh et al., Cancer Res 64:2610-2618, 2004).

HLA-A2/Peptide Tetramer Complexes

Tetrameric MHC class I/peptide complexes were synthesized as described previously (Altman et al., Science 274 (5284):94-96, 1996; Denkberg et al., Proc Natl Acad Sci USA 99(14):9421-9426, 2002). Briefly, purified single-chain HLA-A2 molecules were synthesized by a prokaryotic expression system (pET; R&D Systems, Minneapolis, Minn.). The heavy chain was modified to contain the Bir-A enzymatic biotinylation site. Single-chain heavy chain-β2-microglobulin and peptide were refolded by dilution into a redox-shuffling buffer system. The refolded product was biotinylated by Bir-A in the presence of biotin ligase (Avidity, Denver, Colo.). Streptavidin-phycoerythrin conjugate (Jackson ImmunoResearch, West Grove, Pa.) was added in a 1:4 molar ratio. Per-CP labeled anti-mouse CD8 antibody (BD Pharmingen) and T cell receptor (TCR) VIβ screening panel (BD Pharmingen) were used to detect the TCR repertoire of the CTLs.

Epitope Enhancement

To improve binding of the POTE epitopes to HLA-A2, the sequences for primary and secondary anchor residues that might be suboptimal were examined, based on defined primary and secondary anchors (Ruppert et al., Cell 74:929-937, 1993; Rammensee et al., Immunogenetics 41:178-228, 1995), and peptides with single AA substitutions were synthesized to remedy these deficiencies. These were then tested empirically as described in Example 2 for binding and immunogenicity and for the activity of the CTL induced.

Example 2

Identification and Enhancement of HLA-A2.1-Restricted CTL Epitopes of POTE

Prediction of HLA-A2.1-Restricted Epitopes

The prototype sequence of POTE has 584 amino acid residues. Five 9-mer peptides were first selected based on amino acid anchor residues that determine binding to HLA-A2 molecules and three predictive algorithms (Ruppert et al., *Cell* 74:929-37, 1993; Rammensee et al., *Immunogenetics* 50(3-4):213-219, 1999; Andersen et al., *Scand J Immunol* 57(1): 21-27, 2003; Tourdot et al., *Eur J Imunol* 30(12):3411-3421, 2000). The Parker score is based on a predicted half-time of dissociation to HLA class I molecules using a matrix of AAs at each position in the sequence based on known binding peptides, and a score of higher than 100 is suggested as a potential binder. The second algorithm was developed by Dr. Zhiping Weng, which is based on linear programming for predicting HLA-A2 binding peptides (http://zlab.bu.edu/SMM/). A ln($IC_{50}$) lower than 8 is predicted to be a HLA-A2 binder. The SYFPEITHI score was developed by Hans-Georg Rammensee's lab (http://www.syfpeithi.de/). A SYFPEITHI score higher than 21 predicts a potential HLA-A2 epitope. If the sequence was suggested as a binder by either one of the predictive algorithms, the peptide was used for following study. As shown in Table 1, predictions were not completely consistent among the three algorithms. Therefore, empirical testing and discovery are necessary.

TABLE 1

List of predicted HLA-A2 binders of POTE protein

| Position | Sequence | K Parker score | Z Weng In(IC50) | SYFPEITHI score | $FI_{0.5}$ | SEQ ID NO: |
|---|---|---|---|---|---|---|
| POTE 222-230 | VLMLLEHGA | 31.249 | 3.10 | 19 | 42.4 µM | 2 |
| POTE 252-260 | KLMAKALLL | 276.643 | 6.10 | 24 | 1.6 µM | 3 |
| POTE 272-280 | GLTPLLLGV | 159.970 | 5.30 | 29 | 0.9 µM | 4 |
| POTE 323-331 | LLLEQNVDV | 1793.677 | 4.91 | 28 | 0.8 µM | 5 |
| POTE 553-561 | KILEEIESV | 572.255 | 5.91 | 29 | 5.6 µM | 6 |

Determining the Binding Affinity of POTE Peptides to HLA-A2 Molecules

The binding affinity of the predicted peptides with HLA-A2 molecules was measured by the T2 binding assay. As shown in FIG. 1, POTE 323-331 and POTE 272-280 showed the strongest binding affinity for the HLA-A2 molecule with an $FI_{0.5}$ of 0.8 µM and 0.9 µM, respectively. POTE 252-260 and POTE 553-561 were intermediate binders with the $FI_{0.5}$ of 1.6 µM and 5.6 µM, respectively. Interestingly, none of the three predictive algorithms could perfectly predict the HLA-A2 epitopes, but SYFPEITHI score better agreed with the T2 assay results that POTE 272 is the best binder and POTE 222 is least likely to be an A2 binder. Because POTE 222-230 is a weak binder with an $FI_{0.5}$ around 42.4 µM, this sequence has little chance to bind and be presented by HLA-A2 molecules to $CD8^+$ T cells. Good and intermediate binders were chosen for immunogenicity studies in HLA-A2 transgenic mice.

Epitope Enhancement to Increase the Binding Affinity of POTE Peptides for HLA-A2 Molecules T cells specific for self-peptides with good capacity to bind with MHC class I molecules are frequently negatively selected. Tumor-associated peptides displaying intermediate MHC class I binding affinities might be preferable as vaccine candidates. In addition, their MHC class I binding and immunogenicity can be improved by substitution of primary or secondary anchor amino acids with more optimal binding ones, a procedure named epitope enhancement. Peptides were made with AA substitutions to insert known good primary or secondary anchor residues when these were not already present, based on previous reports (Ruppert et al., *Cell* 74:929-37, 1993; Rammensee et al., *Immunogenetics* 50(3-4):213-219, 1999). Therefore, such modifications were made of intermediate binders, POTE 252 and POTE 553, and again the binding affinity with HLA-A2 molecules was determined by the T2 binding assay. In addition to the intermediate binder, amino acid substitutions were also made in the best binder, POTE 323, to know whether modification could further improve its binding affinity to HLA-A2 molecules. As shown in Table 2, amino acid substitutions in primary (position 2 and the C terminus) or secondary (positions 1, 3 and 7) anchor residues with HLA-A2 molecules were made if they were not optimal (Parker et al., *J Immunol* 152(1); 163-715, 1994; Peters et al., *Bioinformatics* 19(14):1765-1772, 2003).

TABLE 2

List of modified peptides from POTE protein

| Peptide | Sequence | $FI_{0.5}$ | SEQ ID NO: |
|---|---|---|---|
| POTE 252 | KLMAKALLL | 1.5 µM | 3 |
| POTE 252-1Y | YLMAKALLL | 0.9 µM | 7 |

TABLE 2-continued

List of modified peptides from POTE protein

| Peptide | Sequence | $FI_{0.5}$ | SEQ ID NO: |
|---|---|---|---|
| POTE 252-3A | KLAAKALLL | 16.9 µM | 8 |
| POTE 252-3F | KLFAKALLL | 1.5 µM | 9 |
| POTE 252-7A | KLMAKAALL | 4 µM | 10 |
| POTE 252-9V | KLMAKALLV | 0.8 µM | 11 |
| POTE 553 | KILEEIESV | 2.6 µM | 6 |
| POTE 553-1Y | YILEEIESV | 0.024 µM | 12 |
| POTE 553-2L | KLLEEIESV | 0.1 µM | 13 |
| POTE 553-3F | KIFEEIESV | 0.3 µM | 14 |
| POTE-553-7A | KILEEIASV | 0.2 µM | 15 |
| POTE 323 | LLLEQNVDV | 0.3 µM | 5 |
| POTE 323-1Y | YLLEQNVDV | 0.25 µM | 16 |
| POTE 323-3A | LLAEQNVDV | 0.4 µM | 17 |
| POTE 323-3F | LLFEQNVDV | 0.09 µM | 18 |
| POTE 323-7A | LLLEQNADV | 2.78 µM | 19 |

Figure 2A:
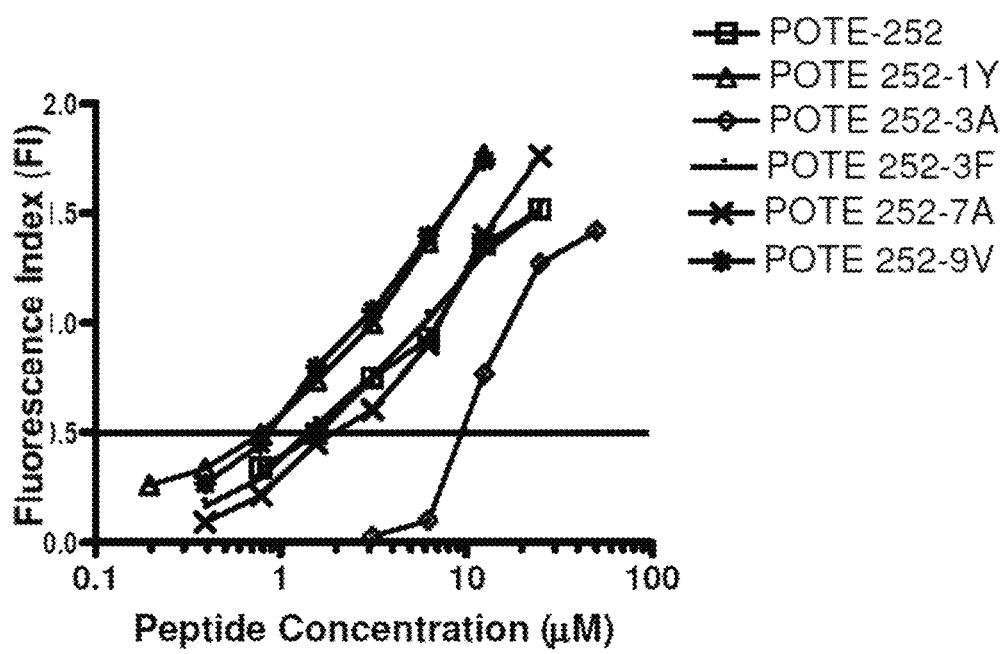
FIGS. 2A-2C are graphs showing binding affinity of substituted POTE peptides to HLA-A2 molecules. Shown are binding affinities of the substituted POTE 252 peptides (FIG. 2A), the substituted POTE 553 peptides (FIG. 2B) and the substituted POTE 323 peptides (FIG. 2C) to HLA-A2 molecules. Different concentrations of peptides were added into the culture of TAP-deficient T2 cells. After overnight culture of the cells in medium supplemented with β2-microglobulin, cells were stained with anti-HLA-A2 antibody. Each assay was performed in triplicate, and data shown in the figures are representative of two experiments with similar results.

Five modified peptides were generated based on the intermediate binder, POTE 252. As shown in FIG. 2A, both POTE 252-9V and POTE 252-1Y had better binding affinity to HLA-A2 molecules than the wild type, POTE 252. The $FI_{0.5}$ of POTE 252-9V and POTE 252-1Y was 0.8 µM and 0.9 µM, respectively. Both were nearly 2-fold lower (higher affinity) than that of the POTE 252 peptide.

Figure 2B:
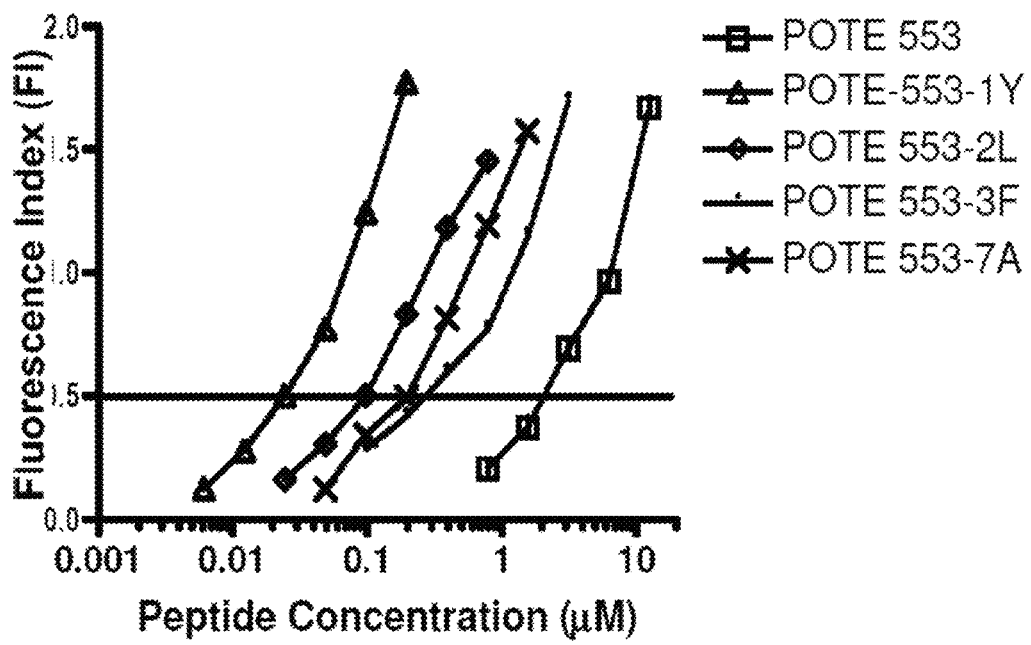

Four substituted peptides were made for another intermediate binder, POTE 553. As shown in FIG. 2B, all of the modified peptides, POTE 553-1Y, POTE 553-2L, POTE 553-7A and POTE 553-3F had better binding affinity to HLA-A2 molecules than the wild type POTE 553 peptide. The $FI_{0.5}$ values of POTE 553-1Y, POTE 553-2L, POTE 553-3F and POTE 553-7A were 0.024 µM, 0.1 µM, 0.3 µM and 0.2 µM, respectively.

Figure 2C:
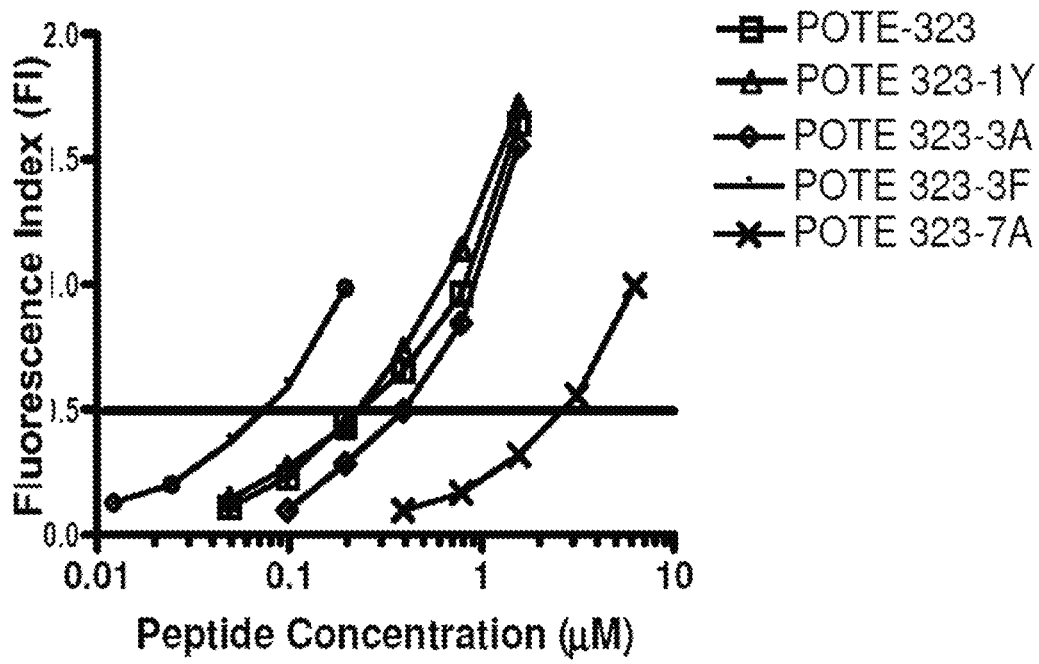

Four peptides were also modified from the best binder, POTE 323. As shown in FIG. 2C, only POTE 323-3F could enhance the binding affinity to HLA-A2 molecules, with the $FI_{0.5}$ of 0.09 µM, about 3-fold better than the wild-type peptide.

Figure 3A:
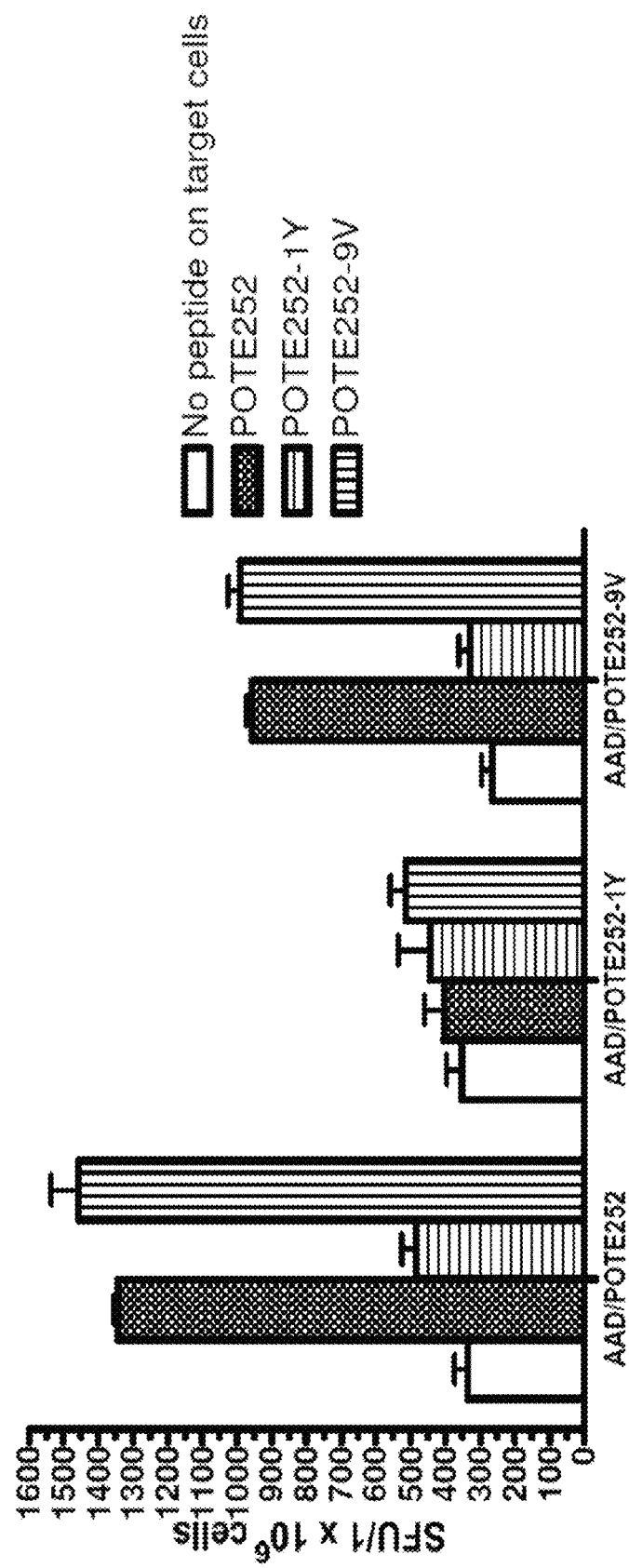
FIGS. 3A and 3B are graphs showing immunogenicity of the wild type and enhanced POTE 252 epitopes in AAD mice. AAD mice were immunized subcutaneously with a mixture of peptide and cytokines in adjuvant as described in Example 1.
Figure 3B:
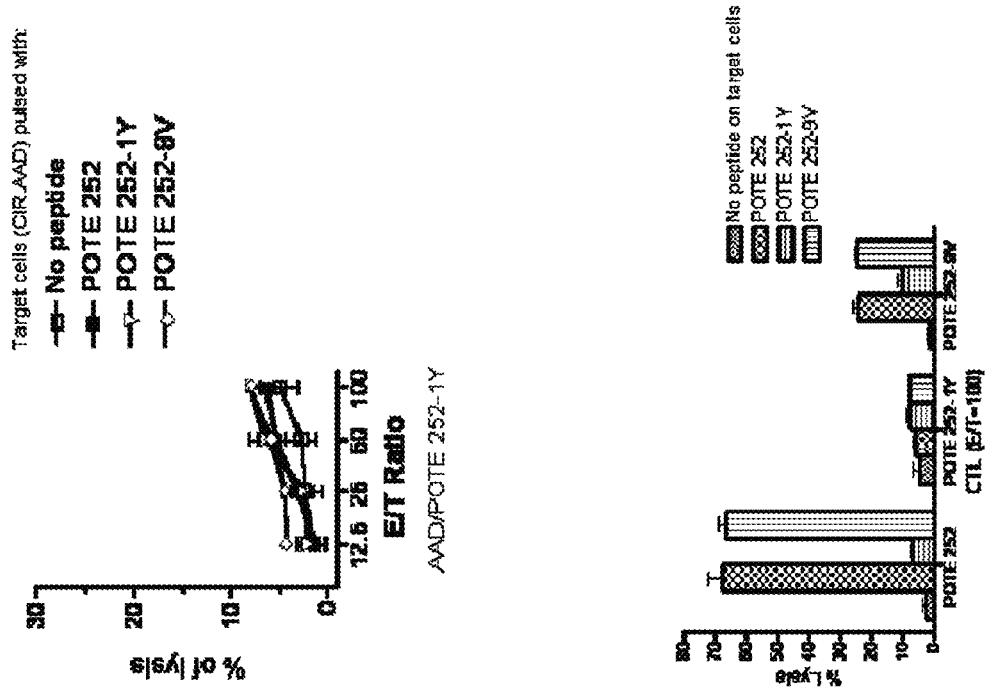
Figure 3B:
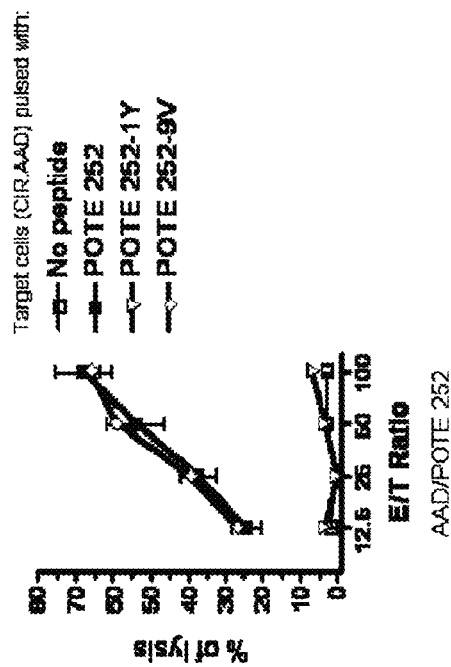
Figure 3B:
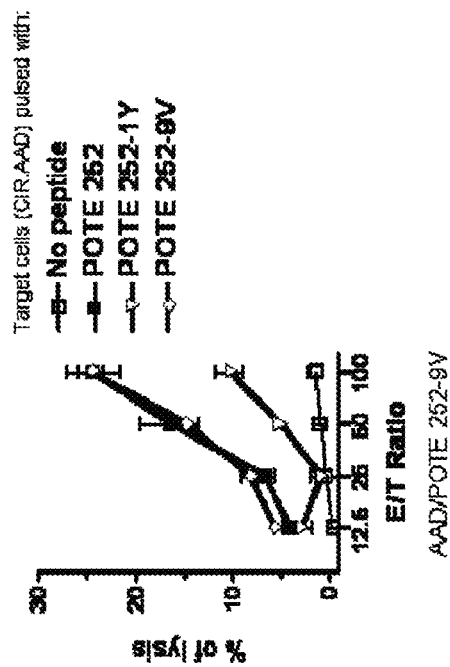

Immunogenicity of the Wild Type and Enhanced POTE 252 Epitopes and CD8+ T-Cell Cross Responses Both POTE 252-9V and POTE 252-1Y had better binding affinity to HLA-A2 molecules than the POTE 252 (FIG. 2A). To test the immunogenicity of wild-type and substituted peptides, and the recognition of the wild-type peptide by CD8+ T cells induced by enhanced peptides, groups of three AAD transgenic mice were immunized with each peptide subcutaneously. Two weeks after the booster, the splenocytes from each group were pooled to measure their immunogenicity by ex vivo IFN-γ ELISPOT™ assay and by CTL assay after one week in vitro stimulation. As shown in FIG. 3A, both POTE 252 and POTE 252-9V induced a significant number of IFN-γ spots with cross reactivity to both POTE 252 and POTE 252-9V. Although POTE 252-1Y had a better binding affinity to HLA-A2 molecules than POTE 252, no significant IFN-γ responses were detected in the assay even in the presence of POTE 252-1Y peptide. After 1-week in vitro stimulation of cognate peptide, CD8+ CTLs induced with both wild type POTE 252 or enhanced epitope POTE 252-9V lysed target cells pulsed with the wild-type POTE 252 as well as POTE 252-9V, suggesting that the TCRs of those CTLs could recognize the wild-type peptide (POTE 252)/MHC class I complex (FIG. 3B). These results were consistent with the ex vivo IFN-γ ELISPOT™ assay. When compared quantitatively, POTE 252 was the most immunogenic peptide in inducing CTL response. POTE 252-9V is also immunogenic in inducing significant CTLs specific for the wild type sequence, POTE 252. Therefore, POTE 252-9V may be a good vaccine candidate to overcome tolerance to target tumor cells expressing POTE.

Figure 4A:
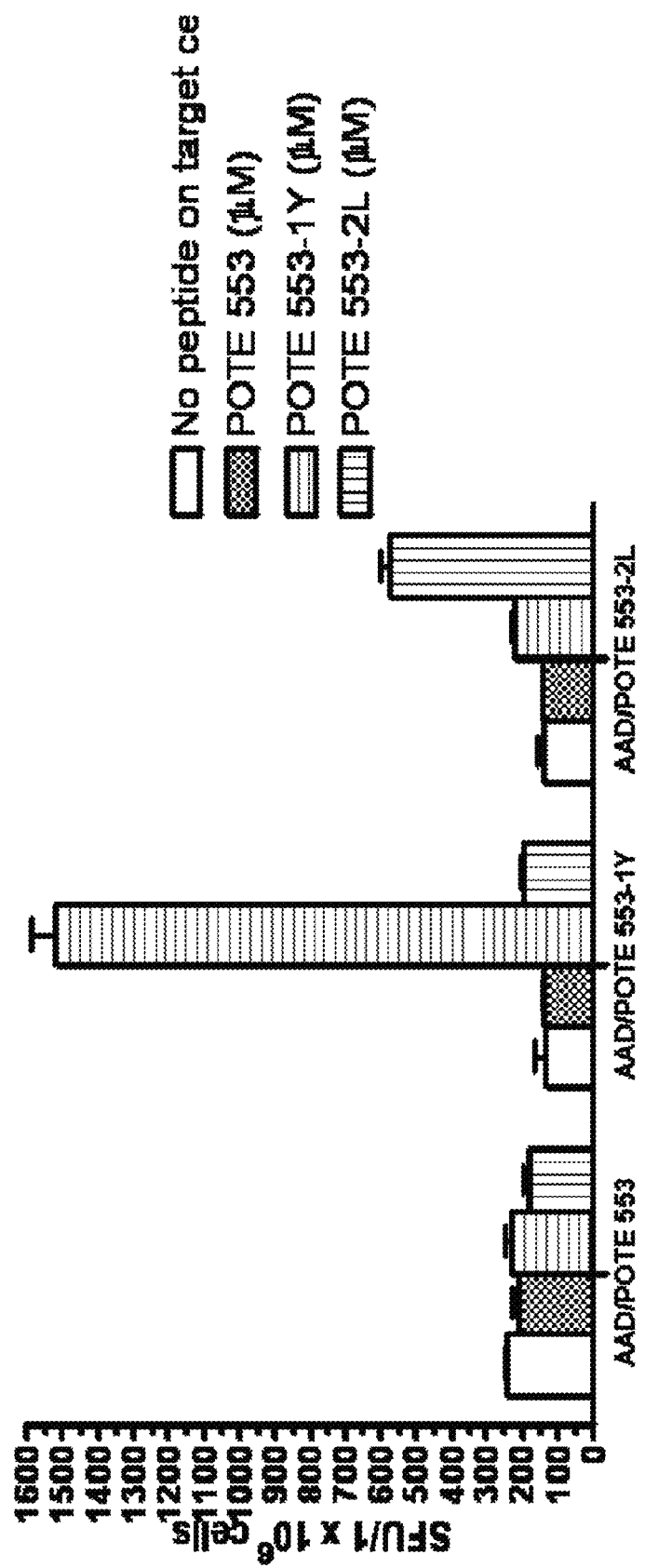
FIGS. 4A-4D are graphs showing immunogenicity of the wild type and enhanced POTE 553 epitopes in AAD mice. AAD mice were immunized subcutaneously with a mixture of peptide and cytokines in adjuvant.
Figure 4B:
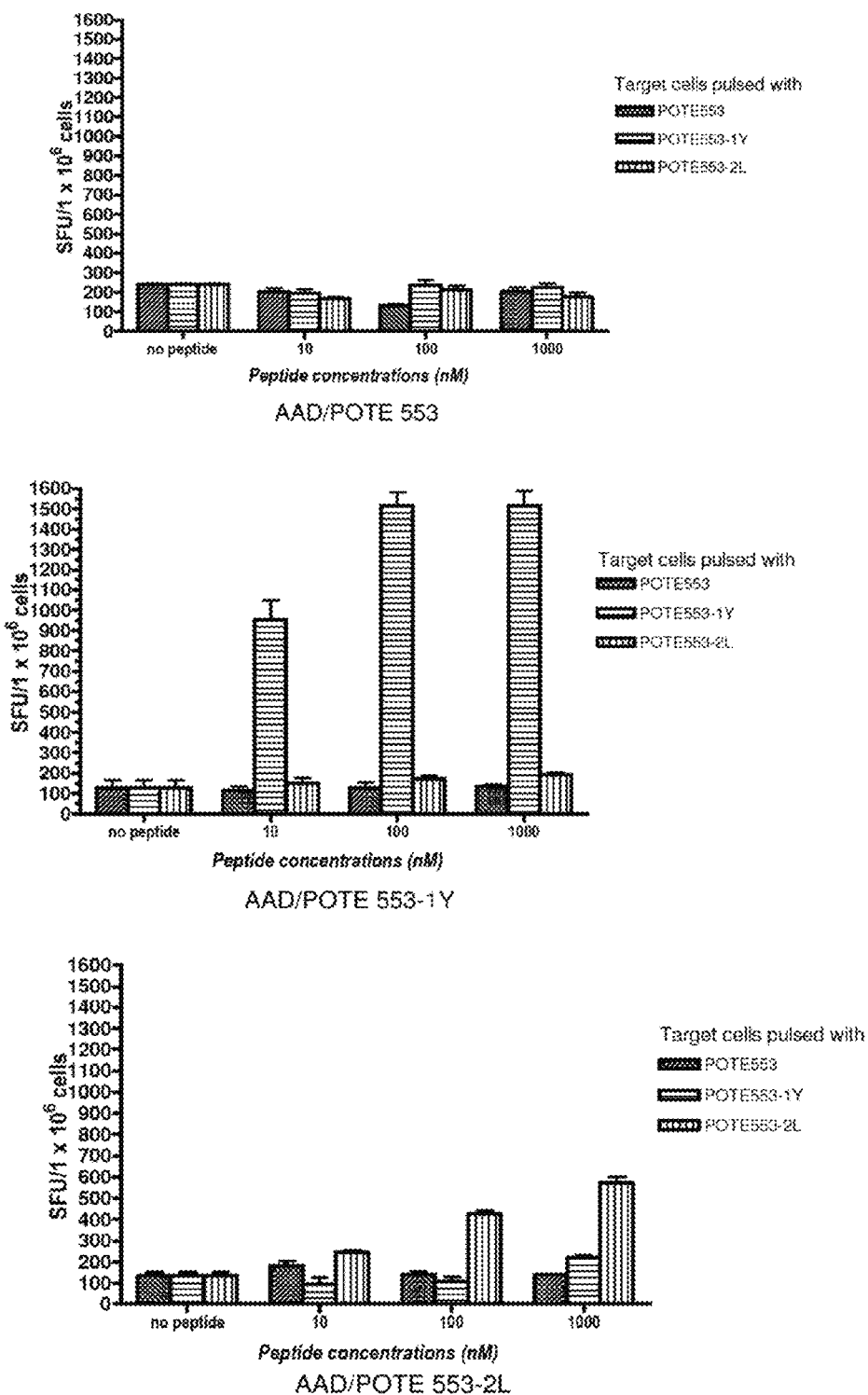
Figure 4C:
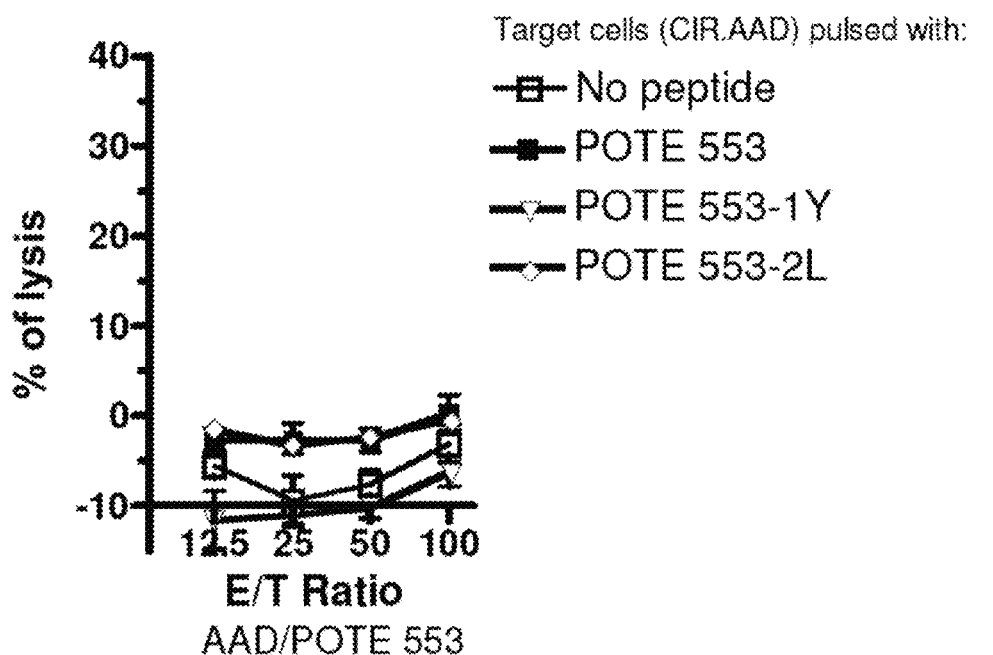
Figure 4C:
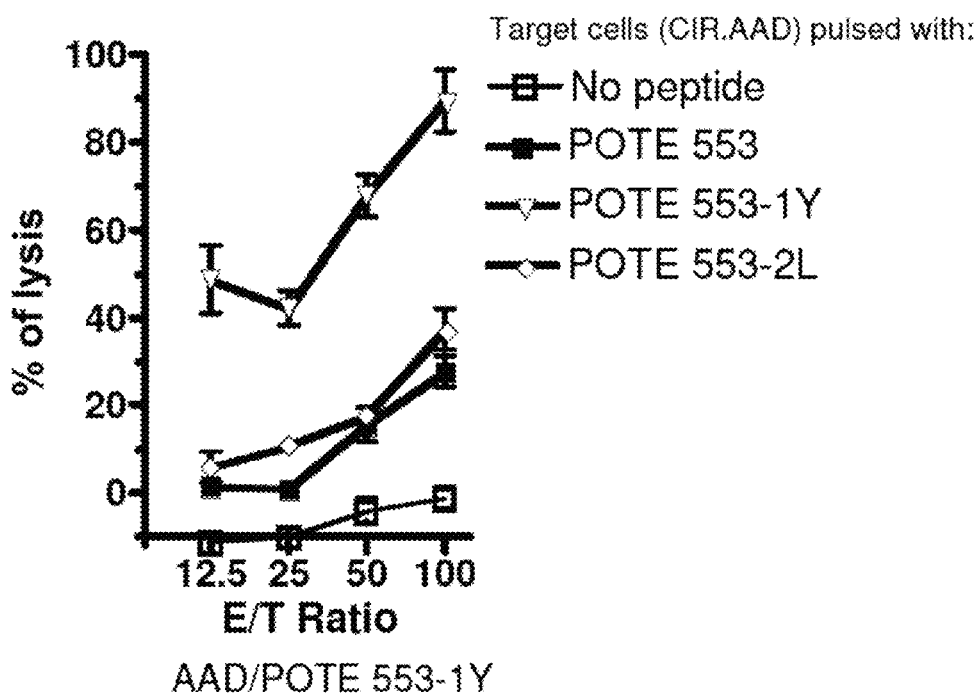
Figure 4D:
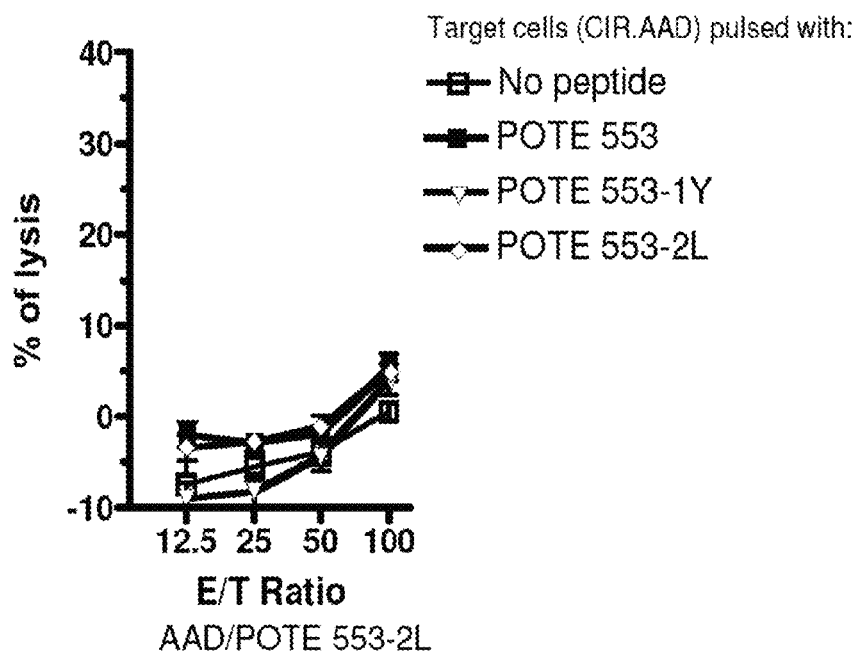
Figure 4D:
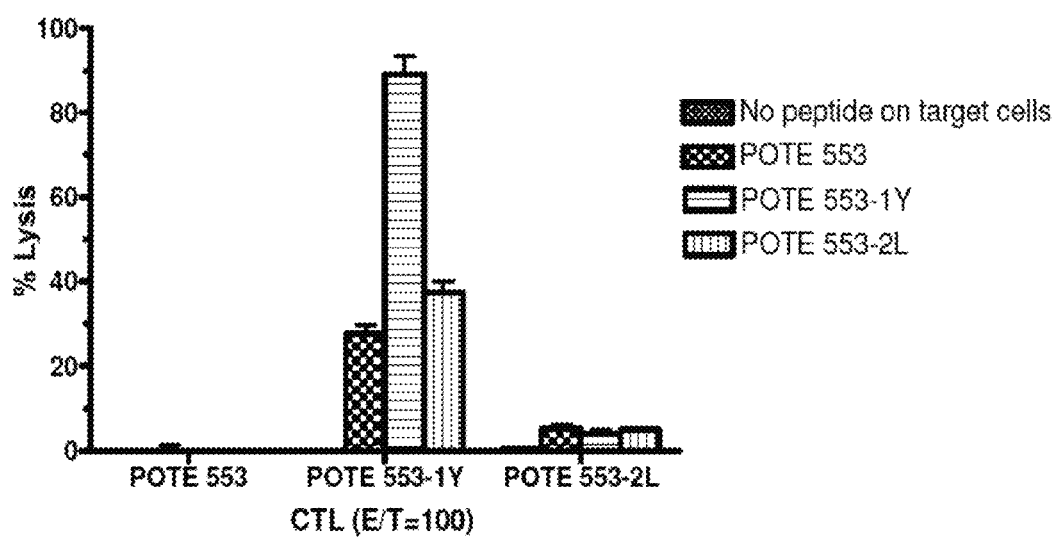

Immunogenicity of the Wild Type and Enhanced POTE 553 Epitopes and CD8+ T-Cell Cross Responses All of the substituted POTE 553 peptides showed better binding affinity to HLA-A2 molecules than the POTE 553 (FIG. 2B). The best two enhanced HLA-A2 binders were chosen, along with the wild-type peptide, to test their immunogenicities and cross-reactive CTL responses. Groups of three AAD transgenic mice were immunized with each peptide subcutaneously. Two weeks after the booster, the splenocytes from each group were pooled to measure their immunogenicity by ex vivo IFN-γ ELISPOT™ assay and by CTL assay after one week in vitro stimulation. As shown in FIGS. 4A and 4B, POTE 553 did not induce any significant IFN-γ responses at any peptide concentration used for stimulation. After one week in vitro stimulation, there was likewise not any significant detectable target cell lysis (FIG. 4C). Therefore, POTE 553, as an intermediate HLA-A2 binder, is not immunogenic. Both POTE 553-1Y and POTE 553-2L induced some extent of IFN-γ responses only after stimulation with the same peptide (FIGS. 4A and 4B). According to the ex vivo IFN-γ ELISPOT™ assay, no cross-reactive response to wild type peptide was detected in the CTLs induced by POTE 553-1Y or POTE 553-2L peptides. However, after one week in vitro stimulation, CD8+ CTLs induced with the enhanced epitope POTE 553-1Y lysed target cells pulsed with not only POTE 553-1Y, but also POTE 553 and POTE 553-2L peptides, suggesting that the TCRs of the CTLs recognize the POTE 553/MHC class I to some extent (FIG. 4C). From this point of view, POTE-553-1Y might be a possible alternative cancer vaccine against the POTE antigen. Although POTE 553-2L can induce certain IFN-γ responses after stimulation with the same peptide (FIGS. 4A and 4B), CD8+ CTLs induced with POTE 553-2L did not lyse target cells pulsed with POTE 553-2L (FIG. 4D). Loss of high-avidity T cells due to antigen-induced cell death during the in vitro stimulation with higher concentration of peptide (1.0 µM) might explain this finding.

Immunogenicity of the Good HLA-A2.1 Binder, POTE 272

Figure 5A:
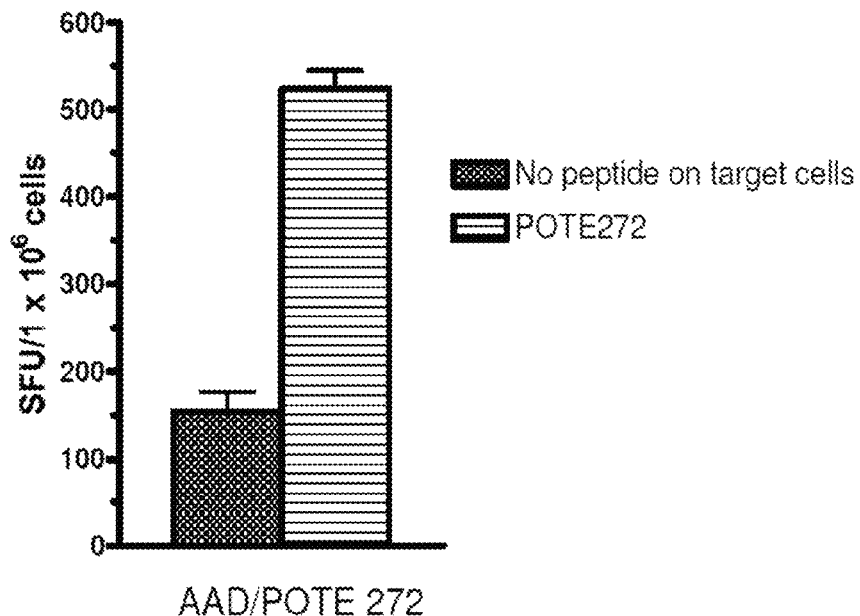
FIGS. 5A and 5B are graphs showing immunogenicity of the POTE 272 epitope in AAD mice. AAD mice were immunized subcutaneously with a mixture of peptide and cytokines in adjuvant.
Figure 5B:
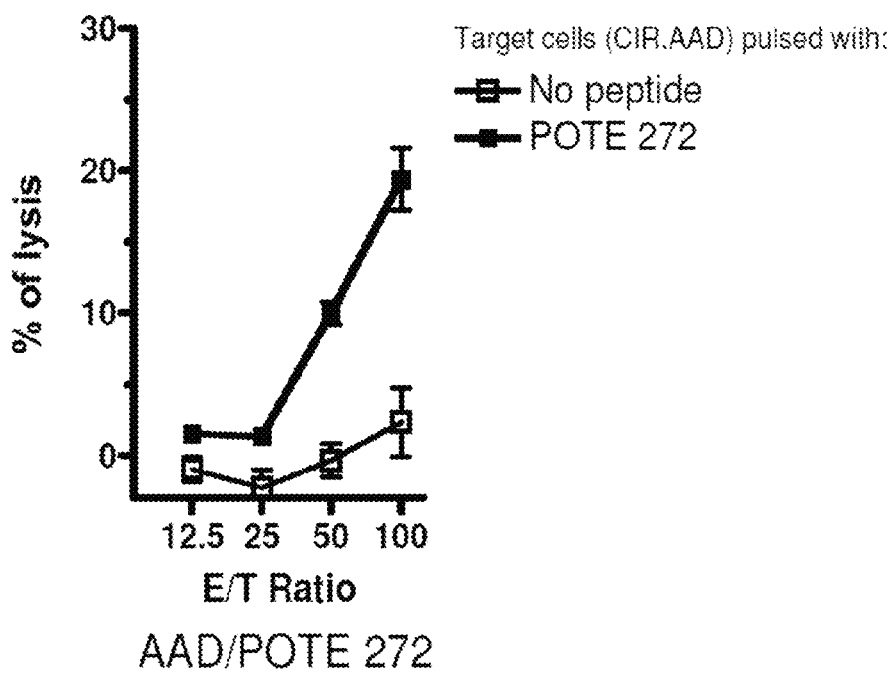

To test the immunogenicity of the POTE 272 peptide, groups of three AAD transgenic mice were immunized with POTE 272 peptide subcutaneously. Two weeks after the booster, the splenocytes from the three mice were pooled to measure their immunogenicity by ex vivo IFN-γ ELISPOT™ assay and by CTL assay after one week in vitro stimulation. As shown in FIG. 5A, POTE 272 induced significant IFN-γ responses under POTE 272 stimulation. After one week in vitro stimulation, CD8+ CTLs induced with POTE 272 lysed target cells pulsed with POTE 272 (FIG. 5B). Therefore, POTE 272 is an immunogenic epitope in the POTE protein.

Figure 6A:
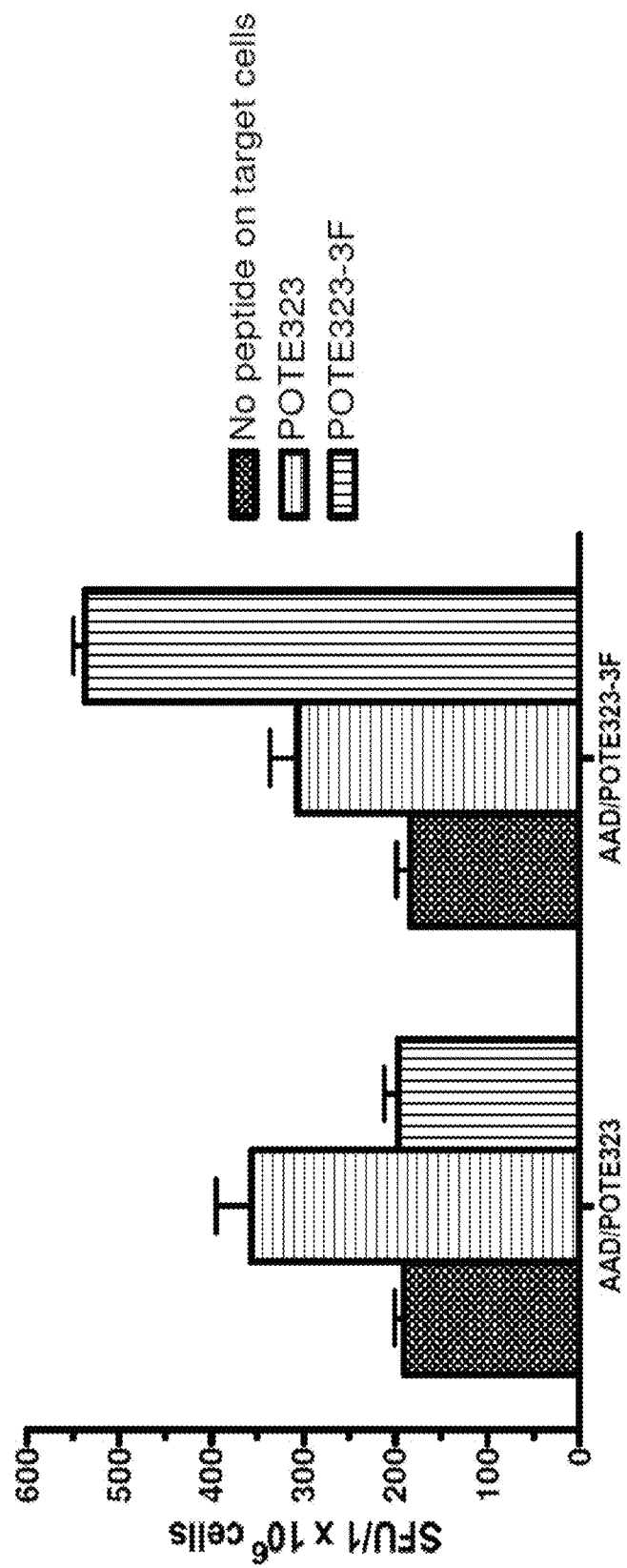
FIGS. 6A and 6B are graphs showing immunogenicity of the wild type and enhanced POTE 323 epitopes in AAD mice. AAD mice were immunized subcutaneously with a mixture of peptide and cytokines in adjuvant.

Immunogenicity of the Wild Type and Enhanced POTE 323 Epitopes and CD8+ T-Cell Cross Responses POTE 323-3F was the only modified peptide with better HLA-A2 binding affinity than wild type POTE 323 (FIG. 2C). To test the immunogenicities of wild-type and substituted peptides, and the recognition of the wild-type peptide by CD8+ T cells induced by the enhanced peptide POTE 323-3F, groups of three AAD transgenic mice were immunized with each peptide subcutaneously. Two weeks after the booster, the splenocytes from each group were pooled to measure their immunogenicity by ex vivo IFN-γ ELISPOT™ assay and by CTL assay after one week in vitro stimulation. As shown in FIG. 6A, both POTE 323 and POTE 323-3F induced some IFN-γ responses after stimulation with the identical peptide. Even though the POTE 323 peptide was the best HLA-A2 binder within the POTE sequence, only marginal IFN-γ responses (less than 2-fold over background level) were detected by the ELISPOT™ assay. After one week in vitro stimulation, CTLs induced by POTE 323 did not lyse target cells pulsed with POTE 323. This negative CTL response might be due to the loss of a substantial portion of responding cells with high avidity that could be killed by incubation with a relatively high concentration of peptide (1.0 µM).

Figure 6B:
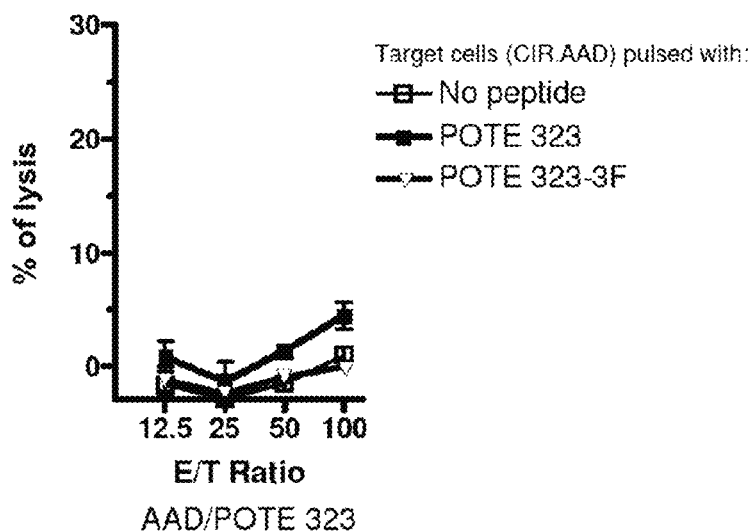
Figure 6B:
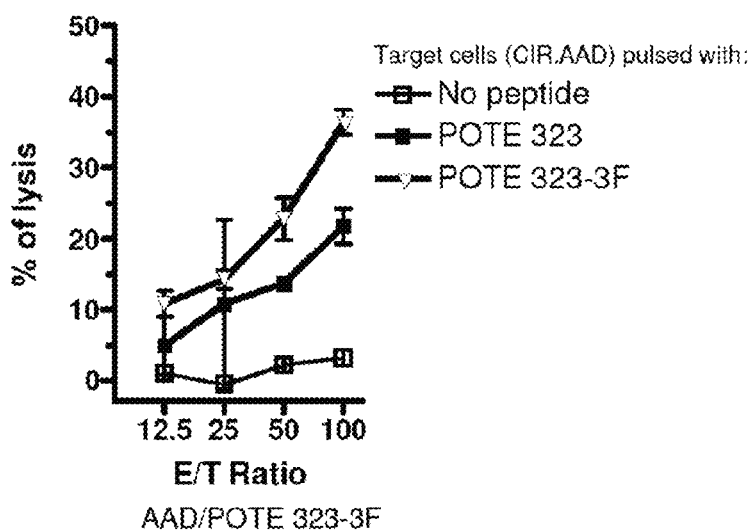
Figure 6B:
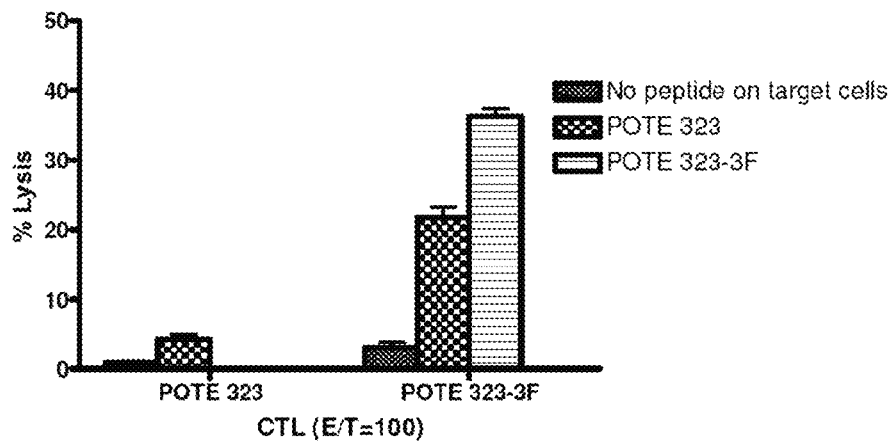

POTE 323-3F induced significant IFN-γ spots under POTE 323-3F stimulation, and some degree of IFN-γ response was also detected after stimulation with wild type POTE 323 epitope. After 1-week in vitro stimulation with the cognate peptide, CD8+ CTLs induced with the enhanced epitope POTE 323-3F lysed target cells pulsed with the POTE 323-3F, as well as wild-type POTE 323, suggesting that the TCRs of the CTLs could recognize the wild-type peptide (POTE 323)/MHC class I complex (FIG. 6B). POTE 323-3F is more immunogenic in inducing CTLs specific for the wild type epitope then is the wild type epitope itself. Therefore, POTE 323-3F is likely to be an excellent vaccine candidate to target tumor cells expressing POTE.

HLA-A2 Tetramer Stain and Analysis of TCR Vβ Repertoire

Figure 7A:
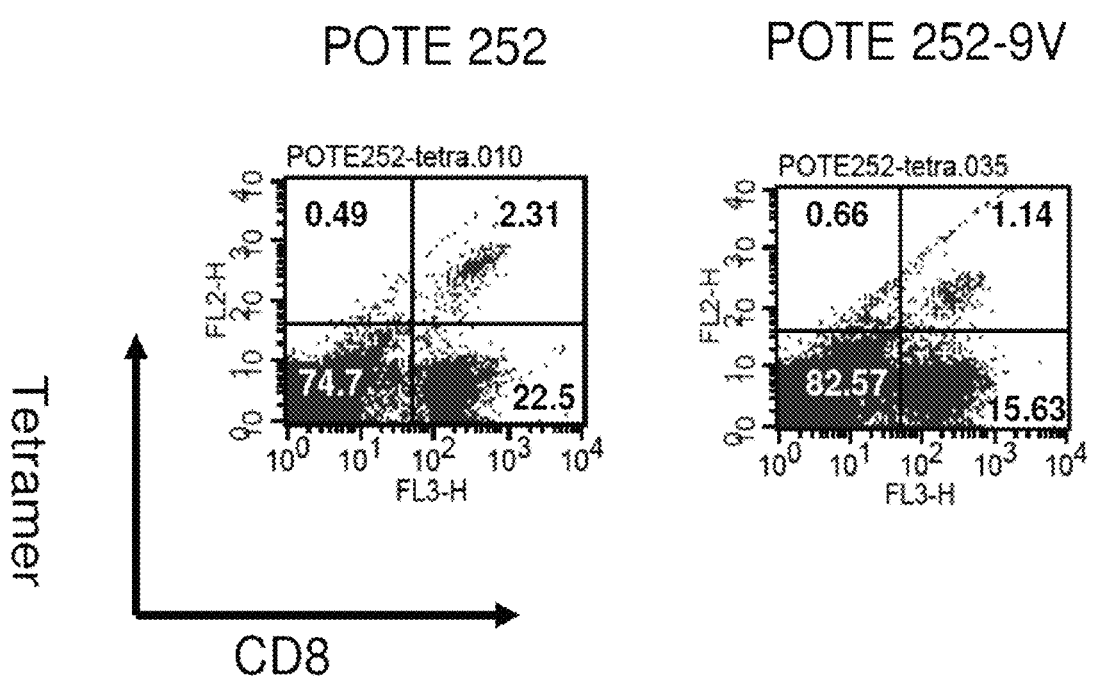
Figure 7C:
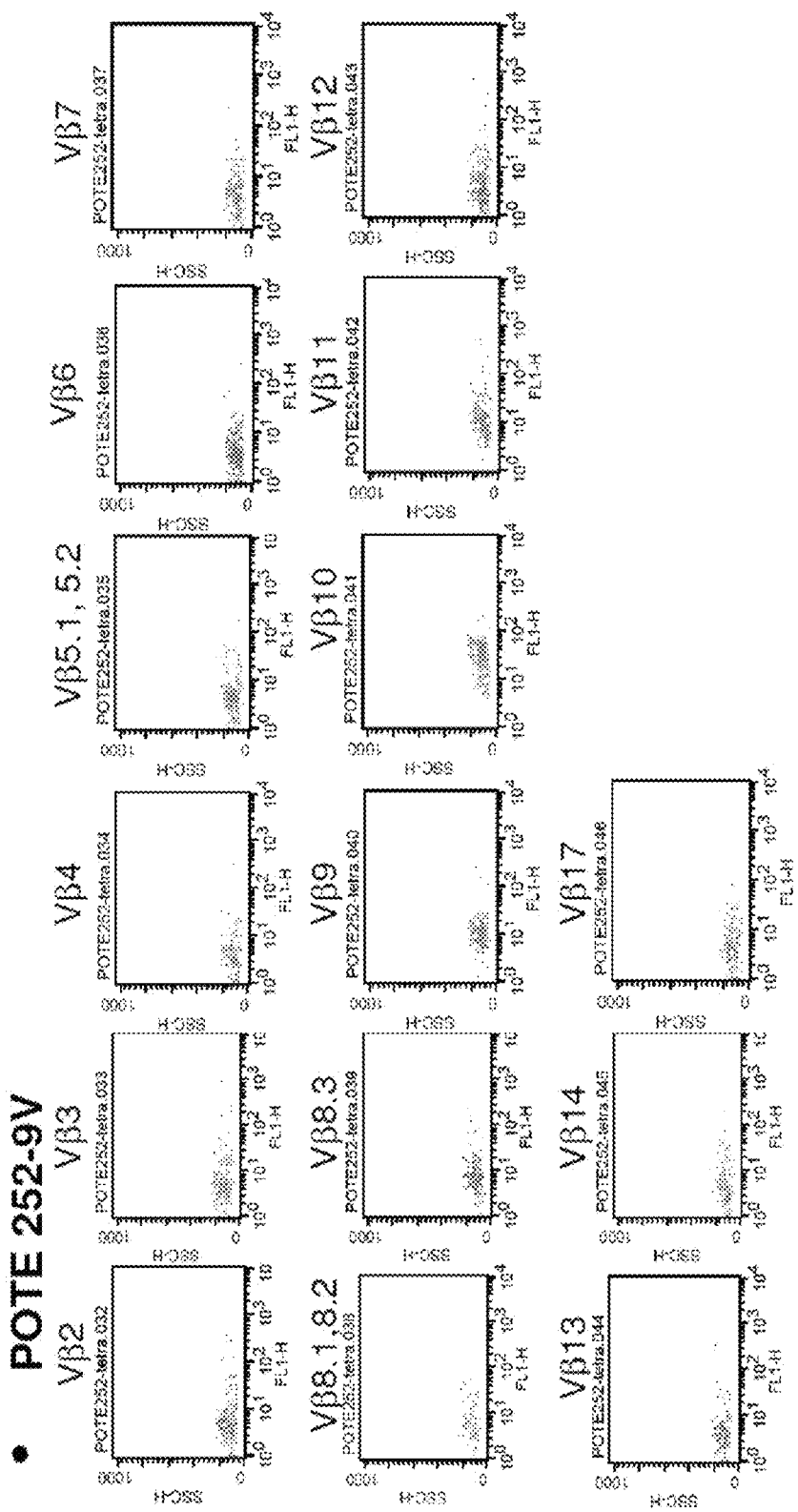

The CTLs induced by POTE 252-9V were the most strongly cross-reactive with wild-type POTE antigen. The response and the TCR repertoire usage of the POTE-specific CD8+ T cells from HHD-2 mice immunized with POTE 252 and 252-9V were further compared. After 1-week in vitro stimulation of cognate peptide, CTLs induced with both wild type POTE 252 or enhanced epitope POTE 252-9V were stained with HLA-A2/POTE252 tetramer, anti-mouse CD8 antibody, and a set of TCR Vβ antibodies. As shown in FIG. 7A, 9.3% versus 6.8% of the CD8+ T cells were tetramer-positive in POTE 252 and POTE 252-9V immunization groups, respectively. By comparing the TCR repertoire of the CD8+tetramer+ T cells between the two groups, the data (FIGS. 7B and 7C) showed that the CTLs induced by POTE 252 were positive for Vβ5.1, 5.2, 6, 7, 8.1, 8.2, 9, 10, 11, whereas the CTLs induced by POTE 252-9V were positive for Vβ 9, 10, and 11. The TCR repertoire of the CD8+tetramer+ T cells were distinct between the wild-type and enhanced POTE peptide immunization.

Summary of Results

In the studies described above, peptide immunogens from POTE protein were defined and the potential of substituted peptides as candidates for the immunotherapy of breast, prostate or other cancers was examined. The first step to develop a cancer vaccine is to identify CD8+ T cell epitopes that can induce immune responses and serve as targets for killing of tumor cells. To define HLA-A2 epitopes from the POTE protein, 9-mer peptides were predicted based on amino acid anchor residues that determine binding to HLA-A2 molecules using three predictive algorithms (Rammensee et al., *Immunogenetics* 50(3-4):213-219, 1999; Gross et al., *J Clin Invest* 113(3):425-433, 2004; Pogue et al., *Proc Natl Acad Sci USA* 92(18):8166-8170, 1995). Based on a T2 binding assay, it appears that none of the predictive algorithms can predict perfectly the rank order of binding affinity to HLA-A2 molecules. Therefore those algorithms can be used for preliminary mass screening only. For the POTE protein, the SYF-PEITHI score best correlated with the experimental binding data.

POTE is composed of over 500 amino acid residues. Among these residues, four 9-mer peptides were defined that had significant binding affinity to HLA-A2 molecules. Most of the tumor antigens are self-antigens, including the POTE protein. CD8+ T cells specific to self-antigens are usually negatively selected in the thymus during T cell development, especially for those with good MHC class I binding affinity (self tolerance). To use a self-antigen as a cancer vaccine target, one possibility is to develop enhanced epitopes that are potentially more immunogenic and against which CD8+ T cells specific to the enhanced epitopes may not be deleted or negatively selected (Okazaki et al., *J Immunol* 171:2548-2555, 2003). More importantly, the TCR specific to enhanced peptide/MHC class I complex should be able to recognize the wild-type peptide/MHC class I complex expressed by the tumor cells.

Amino acid substitutions were first made for intermediate HLA-A2 binders, POTE 252 and POTE 553. Substitution of Leu at position 9 with Val, and Lys at position 1 with Tyr in POTE 252 could improve the peptide binding affinity to HLA-A2 molecules. This could be explained by the optimal amino acid of Val for the last residue, and Tyr in position 1 was reported to stabilize the binding of peptide/MHC complex (Newberg et al., *J Immunol* 156(7):2473-2480, 1996; Tourdot et al. *Eur J Immunol* 30(12):3411-3421, 2000; Shirai et al., *J Immunol* 154:2733-2742, 1995; Rammensee & Bevan, *Nature* 308:741-744, 1984). The immunogenicity of the wild-type and enhanced peptides was compared using AAD and HHD-2 transgenic mice. These mice have been shown to be good predictors of human T cell epitopes (Shirai et al., *J Immunol* 154:2733-2742, 1995). CD8+ CTLs induced with wild type POTE 252 or enhanced POTE 252-9V peptides can recognize cross-reactive POTE252 or POTE252-9V/MHC complexes. The range of TCR recognition induced by both the peptides appeared to overlap substantially in ELISPOT™ and CTL assays. However, the TCR Vβ repertoires of the tetramer+CD8+ T cells were distinct between the POTE252- and POTE 252-9V-induced CTLs. Therefore POTE 252-9V can be a vaccine target for tumors expressing POTE to induce a different repertoire of CTL that might not have been tolerized by the self antigen, but could still cross-react with it. Although POTE 252-1Y can improve the HLA-A2 binding affinity, its immunogenicity was not detectable by ELISPOT™ or CTL assays.

For another intermediate HLA-A2 binder, POTE 553, substitution of Lys at position 1 with Tyr, Ile at position 2 with Leu, Leu at position 3 with Phe, and Glu at position 7 with Ala greatly improved the peptide binding affinity to HLA-A2 molecules. This could be explained by the fact that Leu at position 2 is an optimal HLA-A2 binding sequence (Pogue et al., *Proc Natl Acad Sci USA* 92(18):8166-8170, 1995). Also, amino acid residues associated with poor binding to HLA-A2 are Asp, Glu, Arg, Lys and His at position 7 (Tourdot et al. *Eur J Immunol* 30(12):3411-3421, 2000); consequently, POTE 553-7A can improve the binding affinity to HLA-A2 molecules. Leu at position 3 did not have an adverse effect on HLA-A2 binding affinity, but Phe at position 3 can improve its binding affinity (Okazaki et al., *J Immunol* 171:2548-2555, 2003). In the immunogenicity studies, although POTE 553 is not immunogenic, the enhanced epitope POTE 553-1Y showed greatly improved immunogenicity. CD8+ T cells raised with this epitope can recognize a range of cross-reactive peptide/MHC complexes. Several studies reported that tyrosine substitution at position 1 of an HLA-A2-restricted CTL epitope could increase its binding affinity and did not interfere with TCR interaction (Tourdot et al., *Eur J Immunol* 30(12):3411-3421, 2000; Hahn et al., *Gene* 366(2):238-245, 2006). In the current studies, POTE 252-1Y can increase the HLA-A2 binding affinity, but did not induce immune response. One study showed that 1Y substitution changed the TCR recognition and resulted in the loss of CTL cross reactivity (Okazaki et al., *J Immunol* 171:2548-2555, 2003). Therefore, 1Y substitution did not confer an enhanced immunity in an in vivo study. Nevertheless, it was found that CD8+ T cells induced by POTE-553-1Y cross-reactively recognized wild type POTE 553 peptide/MHC class I complex. This enhanced peptide can also serve as a target for cancer vaccines for tumors expressing POTE.

In the immunogenicity study of the POTE 272 peptide, it showed good binding affinity and induced significant CD8+ T cell responses in AAD mice. Although, self-tolerance may have developed in humans for this self-antigen with good HLA binding affinity, it is immunogenic in the transgenic mice and should be tested for immunogenicity as a cancer vaccine in humans.

POTE 323 is the best HLA-A2 binder among the predicted epitopes. No amino acid residues with adverse effects on HLA-A2 binding affinity existed in its sequence. However, substitution of Leu at position 3 with Phe could further improve the binding affinity to HLA-A2 molecules. Although POTE 323 is the best HLA-A2 binder among the wild type peptide tested, its immunogenicity is not consistent with its binding affinity in the mouse study. One potential explanation was the possibility that mouse POTE and human POTE share the common sequence in this region, so that mouse CD8+ T cells specific to POTE 323 might be negatively selected. However, this possibility can be excluded because the POTE protein is expressed only in primates. The enhanced epitope POTE 323-3F has not only higher binding affinity but also improved immunogenicity. More importantly, CD8+ T cells induced by POTE 323-3F cross-recognized POTE 323/MHC class I complexes. Therefore POTE 323-3F could be a very promising vaccine target for cancers expressing POTE, because the low immunogenicity of the wild type peptide suggests that it may not be tolerogenic either, so an enhanced peptide that elicits T cells cross-reactive with wild type POTE 323 could be effective against POTE-expressing tumor cells. Furthermore, the fact that the POTE 323 peptide induces T cells that make IFN-γ but show poor lytic activity, whereas the POTE 323-3F peptide induces T cells with slightly improved IFN-γ production but much greater lytic activity, suggests that the POTE 323-3F peptide induces a response that is improved in quality as well as quantity.

In consideration of choosing the best target for immunotherapy, POTE 252-9V peptide might be superior to POTE 553-1Y or POTE 323-3F peptides because of a stronger immune response to the wild type sequence detected. However, the combination of POTE 252-9V, POTE 553-1Y and POTE 323-3F epitopes might also be an alternative vaccine strategy to avoid developing immune-escape variants.

Example 3

CTLs Induced by Modified POTE Peptides Against Human Cancer Cells

Figure 8A:
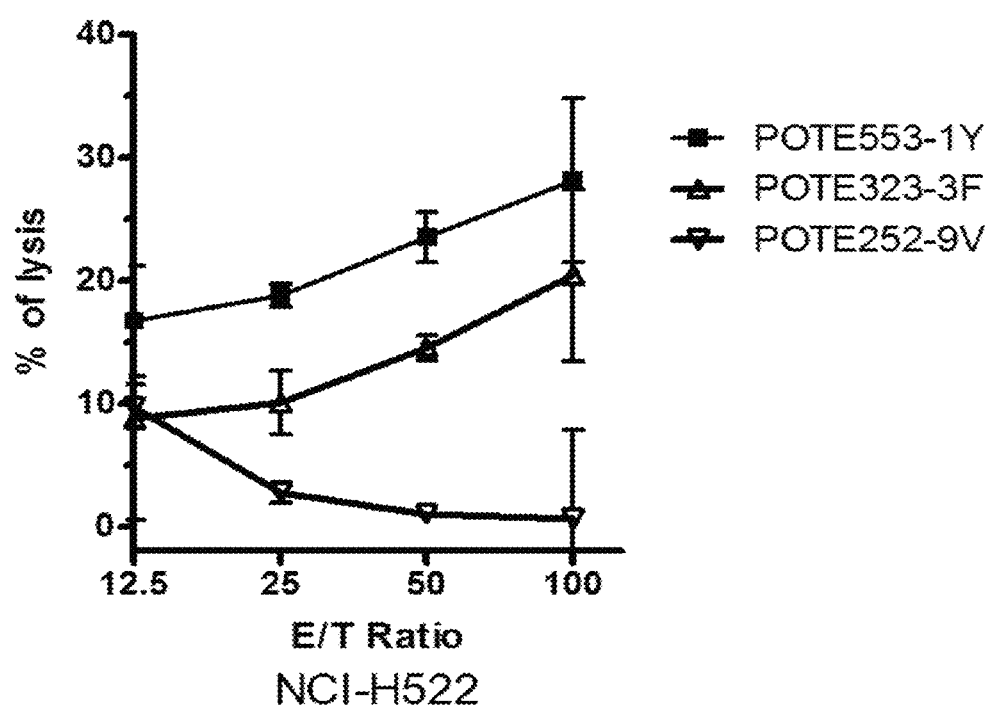
FIGS. 8A-8B are graphs showing anti-tumor cytotoxicity induced by enhanced POTE epitopes. AAD mice were immunized s.c. with 50 nmol of peptide in 100 µl of emulsion.
Figure 8B:
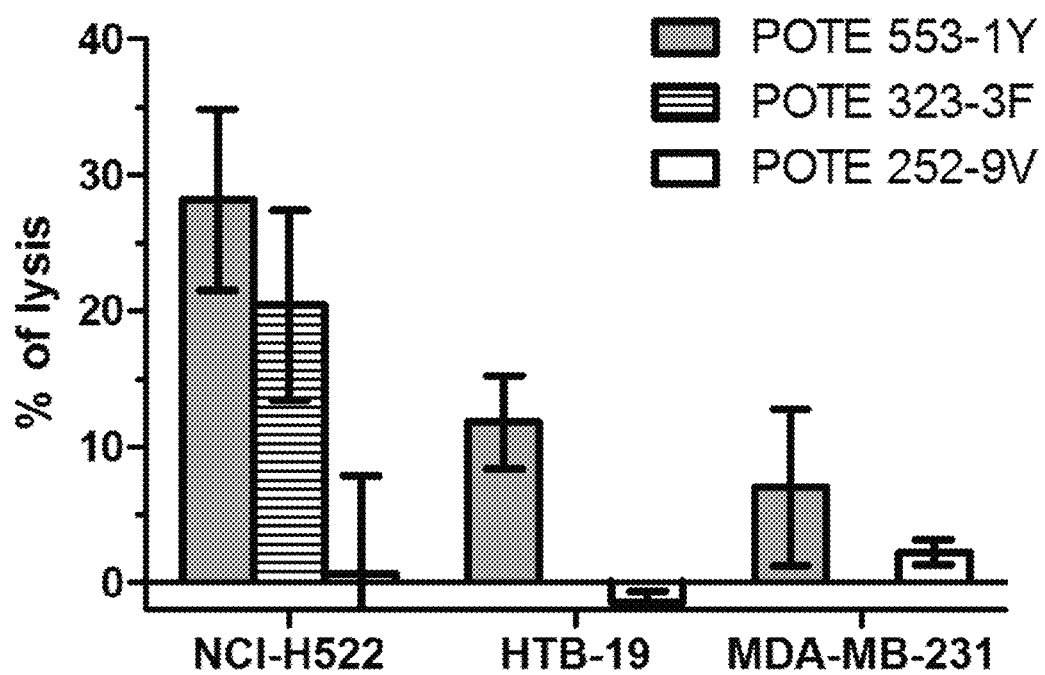

To serve as candidate tumor vaccines, induction of cytotoxicity to kill human cancer cells is essential. Three human cancer cell lines, NCI-H522 (human non-small cell lung cancer cell, POTE+/HLA-A2), HTB-19 (human mammary carcinoma, POTE+/HLA-A1) and MDA-MB-231 (human breast cancer cell, POTE-/HLA-A2) were chosen as target cells in this study. As shown in FIGS. 8A and 8B, although POTE 252-9V is the most immunogenic, the CTLs induced by the modified peptide did not kill POTE-expressing cancer cells, even at high E/T ratios. This suggests that POTE 252 may not be correctly processed and presented on HLA-A2 in these tumor cells. In contrast, the CD8+ T cells induced by both POTE 553-1Y and POTE 323-3F immunization and restimulation produced significant cytotoxicity to lyse NCI-H522 cells. Killing of only the tumors that express both POTE and HLA-A2, and not tumors expressing either one alone, confirms the specificity of the killing for POTE and HLA-A2. These results demonstrate that at least the POTE 553 and 323 epitopes are naturally endogenously processed in human tumor cells and presented on human HLA-A2, and that the epitope-enhanced peptides POTE 553-1Y and 323-3F can induce CTL that recognize the corresponding naturally processed wild type POTE epitopes on human cancer cells.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated nucleic acid molecule encoding an immunogenic polypeptide, wherein the polypeptide comprises no more than 10 consecutive amino acids of the amino acid sequence of human POTE set forth as:

(SEQ ID NO: 20)
MVAEVCSMPTASTVKKPFDLRSKMGKWCHHRFPCCRGSGKSNMGTSG

DHDDSFMKMLRSKMGKCCRHCFPCCRGSGTSNVGTSGDHENSFMKML

RSKMGKWCCHCFPCCRGSGKSNVGAWGDYDHSAFMEPRYHIRREDLD

KLHRAAWWGKVPRKDLIVMLRDTDMNKRDKEKRTALHLASANGNSE

VVQLLLDRRCQLNVLDNKKRTALIKAIQCQEDECVLMLLEHGADRNIPD

EYGNTALHYAIYNEDX$_1$LX$_2$AKAX$_3$LX$_4$YGADIESKNKCGLTPLLLGVHE

QKQQVVKFLIKKKANLNVLDRYGRTALILAVCCGSASIVNX$_5$LX$_6$EQNX$_7$

DVSSQDLSGQTAREYAVSSHHHVICELLSDYKEKQMLKISSENSNPEQD

LKLTSEEESQRLKVSENSQPEKMSQEPEINKDCDREVEEEIKKHGSNPVG

LPENLTNGASAGNGDDGLIPQRRSRKPENQQFPDTENEEYHSDEQNDTR

KQLSEEQNTGISQDEILTNKQKQIEVAEQKMNSELSLSHKKEEDLLRENS

VLQEEIAMLRLELDETKHQNQLRENX$_8$X$_9$X$_{10}$EEIX$_{11}$SVKEKTDKLLRAM

QLNEEALTKTNI, wherein X$_1$ is K or Y; X$_2$ is M, A or F; X$_3$ is L or A; X$_4$ is L or V; X$_5$ is L or Y; X$_6$ is L, A or F; X$_7$ is V, or A; X$_8$ is K or Y; X$_9$ is I or L; X$_{10}$ is L or F; and X$_{11}$ is E or A; and wherein the polypeptide comprises one of (a) amino acids 323-331; (b) amino acids 252-260; or (c) amino acids 553-561 of SEQ ID NO: 20, wherein the polypeptide does not comprise the amino acid sequence KLMAKALLL (SEQ ID NO: 3).

2. The isolated nucleic acid molecule of claim 1, wherein the polypeptide comprises no more than 9 consecutive amino acids of SEQ ID NO: 20.

3. The isolated nucleic acid molecule of claim 1, wherein the polypeptide comprises amino acids 323-331 of SEQ ID NO: 20.

4. The isolated nucleic acid molecule of claim 3, wherein X$_5$ is Y; X$_6$ is A; X$_6$ is F; or X$_7$ is A.

5. The isolated nucleic acid molecule of claim 4, wherein the polypeptide comprises or consists of the amino acid sequence of SEQ ID NO: 18, SEQ ID NO: 16, SEQ ID NO: 17 or SEQ ID NO: 19.

6. The isolated nucleic acid molecule of claim 1, wherein the polypeptide comprises amino acids 252-260 of SEQ ID NO: 20.

7. The isolated nucleic acid molecule of claim 6, wherein X$_1$ is Y; X$_2$ is A; X$_2$ is F; X$_3$ is A; or X$_4$ is V.

8. The isolated nucleic acid molecule of claim 7, wherein the polypeptide comprises or consists of the amino acid sequence of SEQ ID NO: 7, SEQ ID NO: 8, SEQ ID NO: 9, SEQ ID NO: 10 or SEQ ID NO: 11.

9. The isolated nucleic acid molecule of claim 1, wherein the polypeptide comprises amino acids 553-561 of SEQ ID NO: 20.

10. The isolated nucleic acid molecule of claim 9, wherein X$_8$ is Y; X$_9$ is L; X$_{10}$ is F; or X$_{11}$ is A.

11. The isolated nucleic acid molecule of claim 10, wherein the polypeptide comprises or consists of the amino acid sequence of SEQ ID NO: 12, SEQ ID NO: 13, SEQ ID NO: 14 or SEQ ID NO: 15.

12. An isolated nucleic acid molecule encoding a fusion protein comprising an immunogenic POTE polypeptide and a heterologous polypeptide, wherein the immunogenic POTE polypeptide comprises no more than 10 consecutive amino acids of the amino acid sequence of human POTE set forth as:

(SEQ ID NO: 20)
MVAEVCSMPTASTVKKPFDLRSKMGKWCHHRFPCCRGSGKSNMGTSG

DHDDSFMKMLRSKMGKCCRHCFPCCRGSGTSNVGTSGDHENSFMKML

RSKMGKWCCHCFPCCRGSGKSNVGAWGDYDHSAFMEPRYHIRREDLD

KLHRAAWWGKVPRKDLIVMLRDTDMNKRDKEKRTALHLASANGNSE

VVQLLLDRRCQLNVLDNKKRTALIKAIQCQEDECVLMLLEHGADRNIPD

EYGNTALHYAIYNEDX$_1$LX$_2$AKAX$_3$LX$_4$YGADIESKNKCGLTPLLLGVHE

QKQQVVKFLIKKKANLNVLDRYGRTALILAVCCGSASIVNX$_5$LX$_6$EQNX$_7$

DVSSQDLSGQTAREYAVSSHHHVICELLSDYKEKQMLKISSENSNPEQD

LKLTSEEESQRLKVSENSQPEKMSQEPEINKDCDREVEEEIKKHGSNPVG

LPENLTNGASAGNGDDGLIPQRRSRKPENQQFPDTENEEYHSDEQNDTR

KQLSEEQNTGISQDEILTNKQKQIEVAEQKMNSELSLSHKKEEDLLRENS

VLQEEIAMLRLELDETKHQNQLRENX$_8$X$_9$X$_{10}$EEIX$_{11}$SVKEKTDKLLRAM

QLNEEALTKTNI, wherein X$_1$ is K or Y; X$_2$ is M, A or F; X$_3$ is L or A; X$_4$ is L or V; X$_5$ is L or Y; X$_6$ is L, A or F; X$_7$ is V, or A; X$_8$ is K or Y; X$_9$ is I or L; X$_{10}$ is L or F; and X$_{11}$ is E or A; and wherein the polypeptide comprises one of (a) amino acids 323-331; (b) amino acids 252-260; or (c) amino acids 553-561 of SEQ ID NO: 20, wherein the polypeptide does not comprise the amino acid sequence KLMAKALLL (SEQ ID NO: 3).

13. A composition comprising the isolated nucleic acid molecule of claim 1 and a pharmaceutically acceptable carrier.

14. A vector comprising the isolated nucleic acid molecule of claim 1.

15. A composition comprising the vector of claim 14 and a pharmaceutically acceptable carrier.

16. A method of eliciting an immune response in a subject, comprising: (i) selecting a subject in need of treatment; and (ii) administering to the subject a therapeutically effective amount of the nucleic acid molecule of claim 1, thereby eliciting an immune response in the subject.

17. The method of claim 16, wherein the subject in need of treatment is a subject with cancer and the cancer cells express POTE.

18. The method of claim 17, wherein the subject has colon, ovarian, breast, prostate, lung or pancreatic cancer.

* * * * *

SEQUENCE LISTING

```
<160> NUMBER OF SEQ ID NOS: 20

<210> SEQ ID NO 1
<211> LENGTH: 584
<212> TYPE: PRT
<213> ORGANISM: Homo sapiens

<400> SEQUENCE: 1

Met Val Ala Glu Val Cys Ser Met Pro Thr Ala Ser Thr Val Lys Lys
1               5                   10                  15

Pro Phe Asp Leu Arg Ser Lys Met Gly Lys Trp Cys His His Arg Phe
            20                  25                  30

Pro Cys Cys Arg Gly Ser Gly Lys Ser Asn Met Gly Thr Ser Gly Asp
        35                  40                  45

His Asp Asp Ser Phe Met Lys Met Leu Arg Ser Lys Met Gly Lys Cys
    50                  55                  60

Cys Arg His Cys Phe Pro Cys Cys Arg Gly Ser Gly Thr Ser Asn Val
65                  70                  75                  80

Gly Thr Ser Gly Asp His Glu Asn Ser Phe Met Lys Met Leu Arg Ser
                85                  90                  95

Lys Met Gly Lys Trp Cys Cys His Cys Phe Pro Cys Cys Arg Gly Ser
            100                 105                 110

Gly Lys Ser Asn Val Gly Ala Trp Gly Asp Tyr Asp His Ser Ala Phe
        115                 120                 125

Met Glu Pro Arg Tyr His Ile Arg Arg Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Met Asn Lys Arg Asp Lys Glu Lys Arg Thr Ala
                165                 170                 175
```

-continued

```
Leu His Leu Ala Ser Ala Asn Gly Asn Ser Glu Val Val Gln Leu Leu
                180                 185                 190

Leu Asp Arg Arg Cys Gln Leu Asn Val Leu Asp Asn Lys Lys Arg Thr
            195                 200                 205

Ala Leu Ile Lys Ala Ile Gln Cys Gln Glu Asp Glu Cys Val Leu Met
        210                 215                 220

Leu Leu Glu His Gly Ala Asp Arg Asn Ile Pro Asp Glu Tyr Gly Asn
225                 230                 235                 240

Thr Ala Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys Cys Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Val Leu Asp Arg Tyr
290                 295                 300

Gly Arg Thr Ala Leu Ile Leu Ala Val Cys Cys Gly Ser Ala Ser Ile
305                 310                 315                 320

Val Asn Leu Leu Leu Glu Gln Asn Val Asp Val Ser Ser Gln Asp Leu
                325                 330                 335

Ser Gly Gln Thr Ala Arg Glu Tyr Ala Val Ser Ser His His His Val
            340                 345                 350

Ile Cys Glu Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
370                 375                 380

Glu Glu Ser Gln Arg Leu Lys Val Ser Glu Asn Ser Gln Pro Glu Lys
385                 390                 395                 400

Met Ser Gln Glu Pro Glu Ile Asn Lys Asp Cys Asp Arg Glu Val Glu
                405                 410                 415

Glu Glu Ile Lys Lys His Gly Ser Asn Pro Val Gly Leu Pro Glu Asn
            420                 425                 430

Leu Thr Asn Gly Ala Ser Ala Gly Asn Gly Asp Asp Gly Leu Ile Pro
        435                 440                 445

Gln Arg Arg Ser Arg Lys Pro Glu Asn Gln Gln Phe Pro Asp Thr Glu
450                 455                 460

Asn Glu Glu Tyr His Ser Asp Glu Gln Asn Asp Thr Arg Lys Gln Leu
465                 470                 475                 480

Ser Glu Glu Gln Asn Thr Gly Ile Ser Gln Asp Glu Ile Leu Thr Asn
                485                 490                 495

Lys Gln Lys Gln Ile Glu Val Ala Glu Gln Lys Met Asn Ser Glu Leu
            500                 505                 510

Ser Leu Ser His Lys Lys Glu Glu Asp Leu Leu Arg Glu Asn Ser Val
        515                 520                 525

Leu Gln Glu Glu Ile Ala Met Leu Arg Leu Glu Leu Asp Glu Thr Lys
530                 535                 540

His Gln Asn Gln Leu Arg Glu Asn Lys Ile Leu Glu Glu Ile Glu Ser
545                 550                 555                 560

Val Lys Glu Lys Thr Asp Lys Leu Leu Arg Ala Met Gln Leu Asn Glu
                565                 570                 575

Glu Ala Leu Thr Lys Thr Asn Ile
            580
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Val Leu Met Leu Leu Glu His Gly Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Lys Leu Met Ala Lys Ala Leu Leu Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Gly Leu Thr Pro Leu Leu Leu Gly Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Leu Leu Leu Glu Gln Asn Val Asp Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Lys Ile Leu Glu Glu Ile Glu Ser Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Tyr Leu Met Ala Lys Ala Leu Leu Leu
1               5

<210> SEQ ID NO 8
```

```
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Lys Leu Ala Ala Lys Ala Leu Leu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Lys Leu Phe Ala Lys Ala Leu Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Lys Leu Met Ala Lys Ala Ala Leu Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Lys Leu Met Ala Lys Ala Leu Leu Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Tyr Ile Leu Glu Glu Ile Glu Ser Val
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 13

Lys Leu Leu Glu Glu Ile Glu Ser Val
1               5

<210> SEQ ID NO 14
<211> LENGTH: 9
```

```
<212> TYPE: PRT
<213> ORGANISM: Artificial Sequence
<220> FEATURE:
<223> OTHER INFORMATION: Synthetic polypeptide

<400> SEQUENCE: 14

Lys Ile Phe Glu Glu Ile Glu Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 15

Lys Ile Leu Glu Glu Ile Ala Ser Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Tyr Leu Leu Glu Gln Asn Val Asp Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Leu Leu Ala Glu Gln Asn Val Asp Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Leu Leu Phe Glu Gln Asn Val Asp Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 19

Leu Leu Leu Glu Gln Asn Ala Asp Val
1               5

<210> SEQ ID NO 20
<211> LENGTH: 584
<212> TYPE: PRT
```

<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (252)..(252)
<223> OTHER INFORMATION: Xaa = Lys or Tyr
<220> FEATURE:
<221> NAME/KEY: MISC_FEATURE
<222> LOCATION: (254)..(254)
<223> OTHER INFORMATION: Xaa = Met, Ala or Phe
<220> FEATURE:
<221> NAME/KEY: MISC_FEATURE
<222> LOCATION: (258)..(258)
<223> OTHER INFORMATION: Xaa = Leu or Ala
<220> FEATURE:
<221> NAME/KEY: MISC_FEATURE
<222> LOCATION: (260)..(260)
<223> OTHER INFORMATION: Xaa = Leu or Val
<220> FEATURE:
<221> NAME/KEY: MISC_FEATURE
<222> LOCATION: (323)..(323)
<223> OTHER INFORMATION: Xaa = Leu or Tyr
<220> FEATURE:
<221> NAME/KEY: MISC_FEATURE
<222> LOCATION: (325)..(325)
<223> OTHER INFORMATION: Xaa = Leu, Ala or Phe
<220> FEATURE:
<221> NAME/KEY: MISC_FEATURE
<222> LOCATION: (329)..(329)
<223> OTHER INFORMATION: Xaa = Val or Ala
<220> FEATURE:
<221> NAME/KEY: MISC_FEATURE
<222> LOCATION: (553)..(553)
<223> OTHER INFORMATION: Xaa = Lys or Tyr
<220> FEATURE:
<221> NAME/KEY: MISC_FEATURE
<222> LOCATION: (554)..(554)
<223> OTHER INFORMATION: Xaa = Ile or Leu
<220> FEATURE:
<221> NAME/KEY: MISC_FEATURE
<222> LOCATION: (555)..(555)
<223> OTHER INFORMATION: Xaa = Leu or Phe
<220> FEATURE:
<221> NAME/KEY: MISC_FEATURE
<222> LOCATION: (559)..(559)
<223> OTHER INFORMATION: Xaa = Glu or Ala

<400> SEQUENCE: 20

```
Met Val Ala Glu Val Cys Ser Met Pro Thr Ala Ser Thr Val Lys Lys
1               5                   10                  15

Pro Phe Asp Leu Arg Ser Lys Met Gly Lys Trp Cys His His Arg Phe
                20                  25                  30

Pro Cys Cys Arg Gly Ser Gly Lys Ser Asn Met Gly Thr Ser Gly Asp
            35                  40                  45

His Asp Asp Ser Phe Met Lys Met Leu Arg Ser Lys Met Gly Lys Cys
50                  55                  60

Cys Arg His Cys Phe Pro Cys Cys Arg Gly Ser Gly Thr Ser Asn Val
65                  70                  75                  80

Gly Thr Ser Gly Asp His Glu Asn Ser Phe Met Lys Met Leu Arg Ser
                85                  90                  95

Lys Met Gly Lys Trp Cys Cys His Cys Phe Pro Cys Cys Arg Gly Ser
            100                 105                 110

Gly Lys Ser Asn Val Gly Ala Trp Gly Asp Tyr Asp His Ser Ala Phe
            115                 120                 125

Met Glu Pro Arg Tyr His Ile Arg Arg Glu Asp Leu Asp Lys Leu His
        130                 135                 140

Arg Ala Ala Trp Trp Gly Lys Val Pro Arg Lys Asp Leu Ile Val Met
145                 150                 155                 160
```

```
Leu Arg Asp Thr Asp Met Asn Lys Arg Asp Lys Glu Lys Arg Thr Ala
                165                 170                 175

Leu His Leu Ala Ser Ala Asn Gly Asn Ser Glu Val Val Gln Leu Leu
            180                 185                 190

Leu Asp Arg Arg Cys Gln Leu Asn Val Leu Asp Asn Lys Lys Arg Thr
        195                 200                 205

Ala Leu Ile Lys Ala Ile Gln Cys Gln Glu Asp Glu Cys Val Leu Met
210                 215                 220

Leu Leu Glu His Gly Ala Asp Arg Asn Ile Pro Asp Glu Tyr Gly Asn
225                 230                 235                 240

Thr Ala Leu His Tyr Ala Ile Tyr Asn Glu Asp Xaa Leu Xaa Ala Lys
                245                 250                 255

Ala Xaa Leu Xaa Tyr Gly Ala Asp Ile Glu Ser Lys Asn Lys Cys Gly
            260                 265                 270

Leu Thr Pro Leu Leu Leu Gly Val His Glu Gln Lys Gln Gln Val Val
        275                 280                 285

Lys Phe Leu Ile Lys Lys Ala Asn Leu Asn Val Leu Asp Arg Tyr
290                 295                 300

Gly Arg Thr Ala Leu Ile Leu Ala Val Cys Cys Gly Ser Ala Ser Ile
305                 310                 315                 320

Val Asn Xaa Leu Xaa Glu Gln Asn Xaa Asp Val Ser Ser Gln Asp Leu
                325                 330                 335

Ser Gly Gln Thr Ala Arg Glu Tyr Ala Val Ser Ser His His His Val
            340                 345                 350

Ile Cys Glu Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
        370                 375                 380

Glu Glu Ser Gln Arg Leu Lys Val Ser Glu Asn Ser Gln Pro Glu Lys
385                 390                 395                 400

Met Ser Gln Glu Pro Glu Ile Asn Lys Asp Cys Asp Arg Glu Val Glu
                405                 410                 415

Glu Glu Ile Lys Lys His Gly Ser Asn Pro Val Gly Leu Pro Glu Asn
            420                 425                 430

Leu Thr Asn Gly Ala Ser Ala Gly Asn Gly Asp Asp Gly Leu Ile Pro
        435                 440                 445

Gln Arg Arg Ser Arg Lys Pro Glu Asn Gln Gln Phe Pro Asp Thr Glu
450                 455                 460

Asn Glu Glu Tyr His Ser Asp Glu Gln Asn Asp Thr Arg Lys Gln Leu
465                 470                 475                 480

Ser Glu Glu Gln Asn Thr Gly Ile Ser Gln Asp Glu Ile Leu Thr Asn
                485                 490                 495

Lys Gln Lys Gln Ile Glu Val Ala Glu Gln Lys Met Asn Ser Glu Leu
            500                 505                 510

Ser Leu Ser His Lys Lys Glu Glu Asp Leu Leu Arg Glu Asn Ser Val
        515                 520                 525

Leu Gln Glu Glu Ile Ala Met Leu Arg Leu Glu Leu Asp Glu Thr Lys
530                 535                 540

His Gln Asn Gln Leu Arg Glu Asn Xaa Xaa Xaa Glu Glu Ile Xaa Ser
545                 550                 555                 560
```

```
Val Lys Glu Lys Thr Asp Lys Leu Leu Arg Ala Met Gln Leu Asn Glu
            565                 570                 575

Glu Ala Leu Thr Lys Thr Asn Ile
            580
```